US012766013B2

(12) United States Patent
Choi et al.

(10) Patent No.: US 12,766,013 B2
(45) Date of Patent: Oct. 20, 2026

(54) METHOD AND APPARATUS FOR ENHANCING OPERATION OF LEG PROSTHESIS

(71) Applicant: UNIVERSITY OF CENTRAL FLORIDA RESEARCH FOUNDATION, INC., Orlando, FL (US)

(72) Inventors: Hwan Choi, Orlando, FL (US); Sepehr Ramezani, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 637 days.

(21) Appl. No.: 18/268,255

(22) PCT Filed: Dec. 17, 2021

(86) PCT No.: PCT/US2021/063978
§ 371 (c)(1),
(2) Date: Jun. 19, 2023

(87) PCT Pub. No.: WO2022/133181
PCT Pub. Date: Jun. 23, 2022

(65) Prior Publication Data

US 2024/0050246 A1 Feb. 15, 2024

Related U.S. Application Data

(60) Provisional application No. 63/126,683, filed on Dec. 17, 2020.

(51) Int. Cl.
*A61F 2/66* (2006.01)
*A61B 5/00* (2006.01)
(Continued)

(52) U.S. Cl.
CPC ................ *A61F 2/66* (2013.01); *A61B 5/112* (2013.01); *A61B 5/4851* (2013.01); *A61F 2/76* (2013.01); *A61F 2002/7635* (2013.01)

(58) Field of Classification Search
CPC ...... A61F 2/66; A61F 2/76; A61F 2002/7635; A61F 2/74; A61F 2/50; A61F 2002/7655; A61B 5/112; A61B 5/4851
See application file for complete search history.

(56) References Cited

U.S. PATENT DOCUMENTS

2007/0198098 A1* 8/2007 Roston ...................... A61F 2/70 623/57
2008/0300692 A1 12/2008 Moser et al.
(Continued)

FOREIGN PATENT DOCUMENTS

EP 1964982 A1 * 9/2008 ............ E02F 9/2207
WO WO-2018161023 A1 * 9/2018 ............... A61F 2/70

OTHER PUBLICATIONS

PCT search report & written opinion, PCT/US2021/063978, mailed Mar. 11, 2022, 12 pages.
(Continued)

*Primary Examiner* — Nitin Patel
(74) *Attorney, Agent, or Firm* — Timothy H. Van Dyke; Wolter Van Dyke Davis, PLLC

(57) ABSTRACT

A method and an apparatus for enhancing operation of a leg prothesis is provided. The apparatus includes a variable stiffness module configured to be attached between a first portion and a second portion of a leg prothesis. The first portion is configured to move relative to the second portion in a first plane. The variable stiffness module defines an interior region configured to store pressurized fluid. A volume of the interior region is configured to be varied from a first volume to a second volume such that a stiffness of the
(Continued)

variable stiffness module in the first plane is varied from a first stiffness to a second stiffness.

20 Claims, 13 Drawing Sheets

(51) Int. Cl.
*A61B 5/11* (2006.01)
*A61F 2/76* (2006.01)

(56) References Cited

U.S. PATENT DOCUMENTS

| | | | | |
|---|---|---|---|---|
| 2011/0307078 | A1 | 12/2011 | Boender | |
| 2016/0051381 | A1* | 2/2016 | Ásgeirsson | A61F 2/6607 623/26 |
| 2016/0151175 | A1 | 6/2016 | Klute et al. | |
| 2018/0036148 | A1* | 2/2018 | Lincoln | A61F 2/64 |
| 2018/0125679 | A1 | 5/2018 | Kaltenborn et al. | |
| 2022/0370212 | A1* | 11/2022 | Taszreak | A61F 2/66 |

OTHER PUBLICATIONS

Bellman, Ryan D. et al., "SPARKy 3: design of an active robotic ankle prosthesis with two actuated degrees of freedom using regenerative kinetics", Conference Paper, Nov. 2008, 7 pages.
Caldwell, Darwin G. et al., "Control of pneumatic muscle actuators", IEEE Control Systems Magazine, Mar. 1995, pp. 40-48.
Collins, Steven H. et al., "Recycling Energy to Restore Impaired Ankle Function during Human Walking", Plos One, 2010, vol. 5, issue 2, e9307, 6 pages.
DeVita, P. et al., "Effects of asymmetric load carrying on the Biomechanics of walking", J. Biomechanics, 1991, vol. 24, No. 12, pp. 1119-1129.
Elan, www.blatchfordmobility.com/en-us/products/feet-ankles/elen, downloaded from Internet Sep. 13, 2023, 24 pages.
Glanzer, Evan M. et al., "Design and Validation of a Semi-Active Variable Stiffness Foot Prosthesis", IEEE Trans Neural Syst Rehabil Eng., Dec. 2018, vol. 26, No. 12, pp. 2351-2359.
Jin, Li et al., "Modulation of lower extremity joint stiffness, work and power at different walking and running speeds", Human Movement Science, 2018, vol. 58, pp. 1-9.
Liu, May Q. et al., "Muscle contributions to support and progression over a range of walking speeds", J Biomech., Nov. 1, 20084, vol. 41, No. 15, pp. 3243-3252.
Manchola, Miguel et al., "T-FLEX: Variable Stiffness Ankle-Foot Orthosis for Gait Assistance", Biosysrob, 2019, vol. 22, pp. 160-164.
Mooney, Luke M. et al., "Design and Characterization of a Biologically Inspired Quasi-Passive Prosthetic Ankle-Foot", IEEE, 2014, pp. 1611-1617.
Mrazsko, Hannah X., "Design of a Variable Stiffness Pneumatic Ankle Prosthesis With Self- Recharging for Weightlifting Exercise", Journal of Medical Devices, Sep. 2020, vol. 14, 034501-1-034501-7.
Pro-Flex XC Torsion, Ossur.com, downloaded from Internet Sep. 13, 2023, 8 pages.
Sepp, Lauren A. et al., "Running-Specific Prostheses Reduce Lower-Limb Muscle Activity Compared To Daily-Use Prostheses in People With Unilateral Transtibial Amputations", Elsevier, 2020, 25 pages.
Shepherd, Max K. et al., "The VSPA Foot: A Quasi-Passive Ankle-Foot Prosthesis With Continuously Variable Stiffness", IEEE Transactions On Neural Systems and Rehabilitation Engineering, Dec. 2017, vol. 25, No. 12, pp. 2375-2386.
Symeonidis et al., "Simulation of Biomechanical Experiments in OpenSim", IFMBE Proceedings, MEDICON, 2010, vol. 29, pp. 107-110.

* cited by examiner

Ankle assistive device stiffness (AADS) test

Pneumatic and hydraulic variable stiffness system bench test setup (left). Static test results in no pre-charge conditions. Asterisk, cross, and circle symbols demonstrate experimental results. Solid lines demonstrate simulation results. (right).

METHOD AND APPARATUS FOR ENHANCING OPERATION OF LEG PROSTHESIS

CROSS-REFERENCE TO RELATED APPLICATIONS

This application claims benefit of Provisional Appln. 63/126,683, filed 17 Dec. 2020, the entire contents of which are hereby incorporated by reference as if fully set forth herein, under 35 U.S.C. § 119(e).

BACKGROUND

Over 1.6 million people in the United States are living with lower limb amputation. This number is rising and is expected to double by 2050. Transtibial amputation, or below-knee amputation, has multiple disadvantages due to the loss of most of the calf muscle. Calf muscles, particularly the gastrocnemius and soles muscles, play an important role in supporting the body and propelling it forward.

SUMMARY

Passive ankle foot prostheses are widely used due to their low cost, durability, and light weight. The main feature of these devices is their ability to recycle energy during walking. For example, from heel contact to midstance, the carbon fiber foot deforms from the body weight. As the center of mass of the body moves forward in the transition from midstance to terminal stance, the foot starts to return to its original shape, providing support and propulsion energy that was stored in the deformation of the foot. This mechanism of energy recycling is comparable with the calf muscles and Achilles tendon. The musculotendon function of an unimpaired individual can accommodate various walking conditions by manipulating the biological ankle's stiffness and energy return timing to optimally support and propel the body forward. However, the inventors of the present invention recognized downsides of this design. For example, the prostheses made with a carbon fiber blade, the most widely available design, only provide a single stiffness and has no ability to control the energy release timing, leading to improper walking behaviors, i.e., walking asymmetry, increased musculature demands, and excessive joint loads in different walking conditions [1], [2]. Thus, the inventors of the present invention recognized that it is important to have ankle prostheses which can rapidly alter their ankle stiffness to provide efficient and comfortable walking for people with lower limb amputation.

To improve upon single stiffness of ankle foot prostheses by providing an adaptable stiffness under various walking conditions, several semi active prosthetic designs which can alter the stiffness using a combination of elastic components and microprocessors have been suggested. For example, some conventional systems use a tension spring to adjust the torque-angle curve by applying pretension [3], [4]. The inventors of the present invention also recognized downsides of this design. Although the pretension of the spring can provide a fixed increase to the torque applied by the prosthesis, the level of stiffness (the slope of the torque-angle curve) does not change due to the intrinsic character of the applied spring. In order to manage the energy recycling of the prosthetic ankle joint, a highly stiff spring is required and providing pretension from this spring requires powerful actuators which leads to increases in device weight and size. Three-point bending of linear carbon fiber bar has also been suggested to control the level of stiffness [5], [6]. The fulcrum slides along a carbon fiber beam and creates the lowest stiffness when positioned toward the bending point. As the position of the fulcrum deviates from the bending point, the level of stiffness increases. This type of design can provide continuously adaptable stiffness; however, it requires having a stiff foot to maintain the fulcrum rail alignment. In addition to this, the maneuvering speed of the fulcrum may not be fast enough to change the stiffness because the movement of the fulcrum is coupled with an acme screw and requires many rotations of acme screw to move.

The use of a hydraulic cylinder is another approach to modulating the level of stiffness. Commercially available ankle foot prostheses are known that employ hydraulic components to the carbon fiber foot blade [7], [8], [9]. They are designed to adjust the level of impedance on the ankle joint using a hydraulic component to provide custom stiffness or absorb impact during heel contact to improve stability. The inventors of the present invention also recognized one or more downsides of this design. Although the hydraulic cylinders of these prostheses can adjust the level of ankle impedance, they typically act as resistive components that dissipate energy and cannot modulate energy return as they still have a pre-set single stiffness carbon fiber blade that manages energy return [10]. Pneumatic actuators and pneumatic cylinders behave similarly to mechanical springs and have the potential for enabling adjustable stiffness in a prosthesis. For example, pneumatic driven muscle-like actuators are another way to control ankle prostheses [11]. The pneumatic actuators are typically grouped in pairs, an agonist and an antagonist, to control plantarflexion and dorsiflexion because the actuators cannot generate contractile force. As a result, the set of actuators require a larger space than using a single pneumatic cylinder and consume greater amounts of pressurized air.

Prosthetic designs with a pneumatic cylinder also use pressurized air to store energy. Such designs include a semi-active mechanism to provide a wide range of motion for different activities [12]. The pneumatic cylinder compresses and stores energy during dorsiflexion of the ankle, which it returns to the user when the ankle is straightened. When higher pressure is needed to employ a high level of ankle stiffness, an external pressure source, a bike pump, is needed to increase the pressure of the cylinder and reservoir. When a lower pressure is needed, air is manually released from its pressurized chamber. However, in this design, an initial pressure is set and remains fixed during motion. Over time, the chamber will depressurize, and an external pressure supply is needed to recharge the cylinder and reservoir. Another disadvantage of this concept is when the operator increases cylinder pressure, the stable angle of the ankle will change and an unwanted moment will be applied to the body during the stance phase.

To avoid the challenges of integrating an external pressure source, a closed-loop pneumatic system has been suggested to control the stiffness of prosthesis. Such systems use a pneumatic orifice to control the flow of air into the pneumatic cylinder [13]. Dorsiflexion of the ankle joint during mid-terminal stance transfers air into the pneumatic cylinder through the orifice. The diameter of the orifice connecting the pneumatic both sides of the cylinder is modulated, controlling the flow rate of air between two sides of the cylinder and thus the impedance of prosthesis. In fact, changing the flow rate throw the orifice acts as a damper and dissipates energy rather than storing energy resulting in no energy return.

The inventors of the present invention recognized that controlling the level of air pressure and the timing of the release of the pressurized air of the pneumatic cylinder would potentially control of the level of stiffness and energy return timing, respectively. Although employing an external energy supply source (i.e., compressor) allows for this degree of control of the pneumatic cylinder, the inventors of the present invention recognized that compressors are generally heavy, bulky and noisy, so it may be extremely challenging to integrate them into a portable prosthesis which needs to be lightweight and have a compact size for practical use in daily living. Thus, the inventors of the present invention propose a semi-active ankle foot prosthesis that is capable of adjusting stiffness and energy return timing in real time using a hybrid closed loop pneumatic and hydraulic system that can be compact, lightweight, and energy efficient.

In one embodiment, an apparatus is provided for enhancing operation of a leg prothesis. The apparatus includes a variable stiffness module configured to be attached between a first portion and a second portion of a leg prothesis. The first portion is configured to move relative to the second portion in a first plane. The variable stiffness module defines an interior region configured to store pressurized fluid. A volume of the interior region is configured to be varied from a first volume to a second volume such that a stiffness of the variable stiffness module in the first plane is varied from a first stiffness to a second stiffness.

In another embodiment, a method is provided for enhancing operation of a leg prothesis. The method includes attaching a variable stiffness module between a first portion and a second portion of a leg prothesis. The method also includes moving, in a first plane, the first portion relative to the second portion. The method also includes adjusting a volume of an interior region configured to store pressurized fluid within the variable stiffness module from a first volume to a second volume such that a stiffness of the variable stiffness module in the first plane varies from a first stiffness to a second stiffness.

In another embodiment, a leg prosthesis is provided with an apparatus according to the above embodiment mounted thereon.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

Figure 1A:
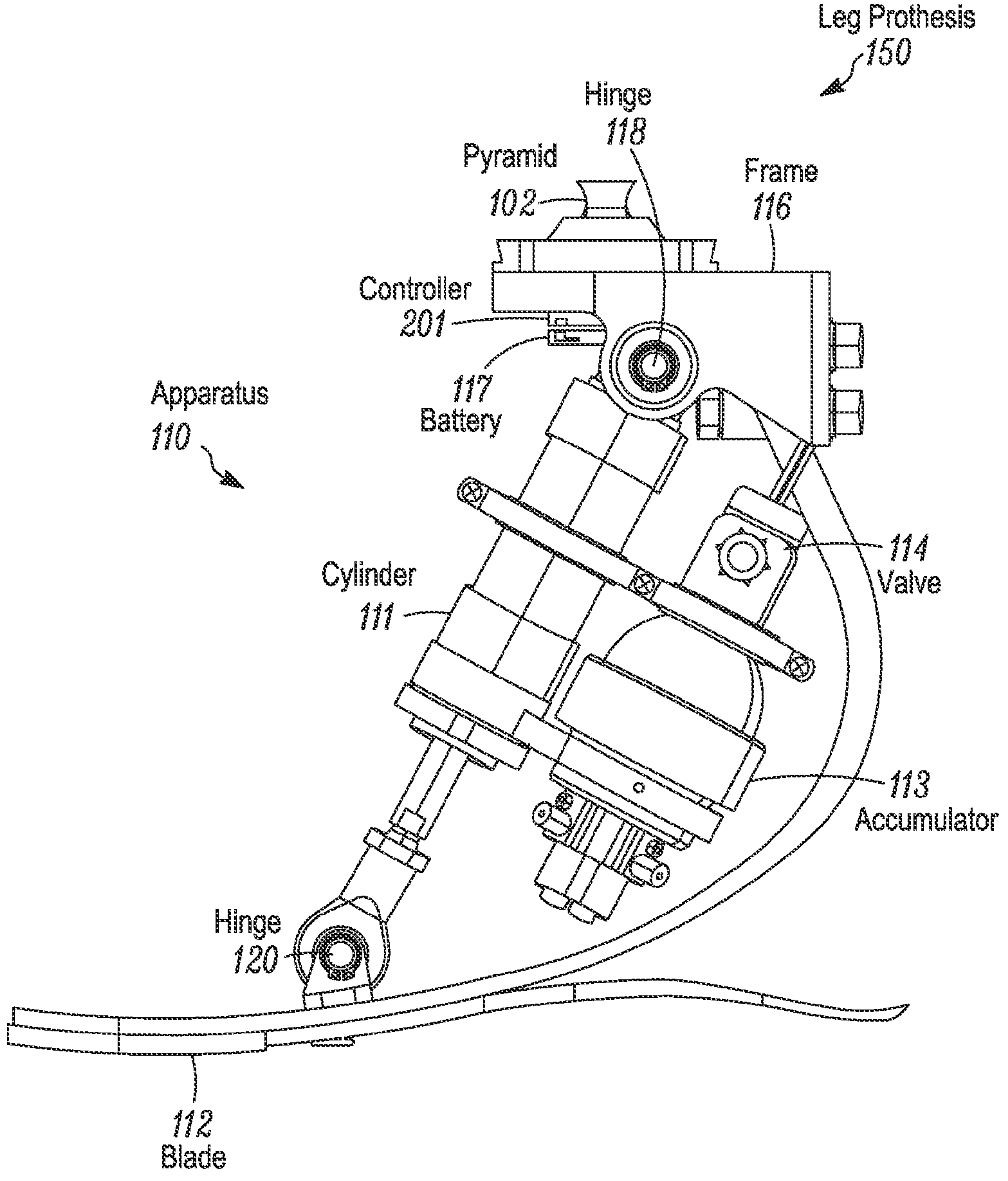
FIG. 1A is an image that illustrates an example of a side view of a system for enhancing an operation of a leg prothesis, according to an embodiment.

A method and apparatus are described for enhancing the operation of leg prostheses and/or ankle protheses. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of enhancing the operation and functionality of leg protheses and/or ankle protheses. For purposes of this invention, "leg protheses" means one or more artificial body parts to replace any part of the leg and/or foot of a subject (e.g., human or non-human) that is not present (e.g., amputated). In an example embodiment, the leg protheses is one or more artificial body parts that replace one or more portions of the leg below the knee (e.g., for a transtibial amputation). In still other embodiments, the leg protheses is one or more artificial body parts that replace one or more portions of the leg above the knee (e.g., for subjects with above knee amputation). In other embodiments, the invention is described below in the context of improving the timing of stiffness adjustment of the leg prothesis based on conditions of movement (e.g., gait phase, speed of movement, incline of movement, surface of movement, etc.) of the user of the leg prothesis. In still other embodiments, the invention is described below in the context of a design of a variable stiffness module that can be applied to prosthetic devices (e.g., prosthetic foot, prosthetic knee or arm, etc.).

1. Overview

Figure 1B:
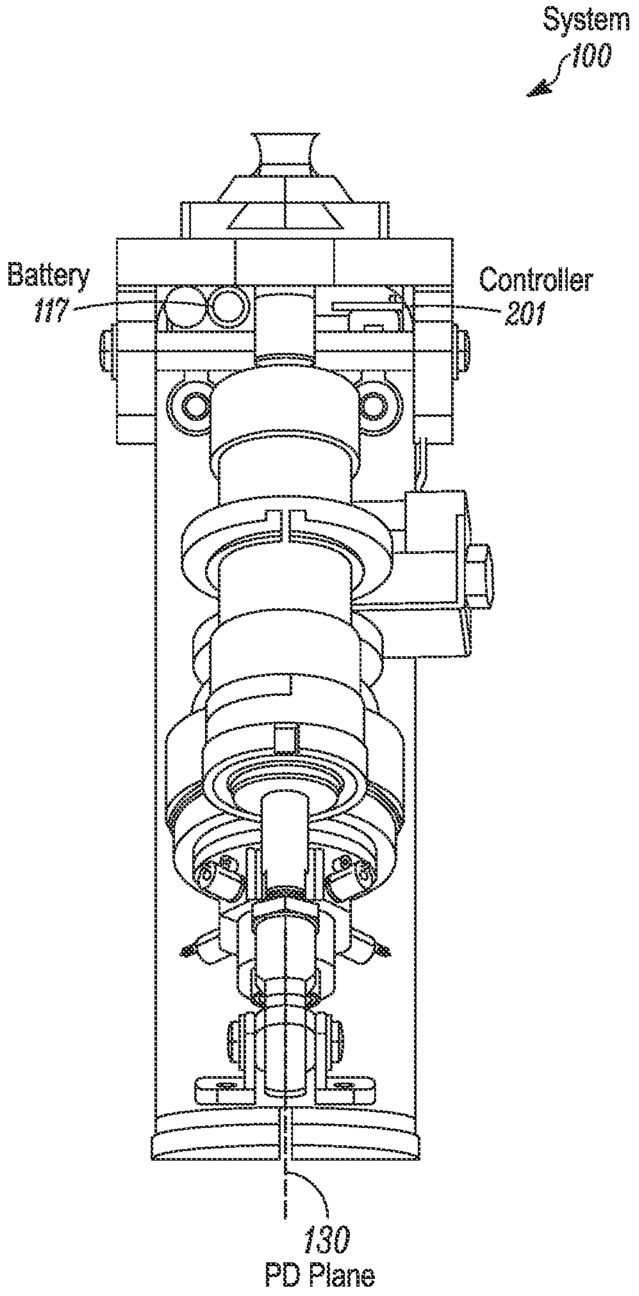
FIG. 1B is an image that illustrates an example of a front view of the system of FIG. 1A, according to an embodiment.
Figure 1C:
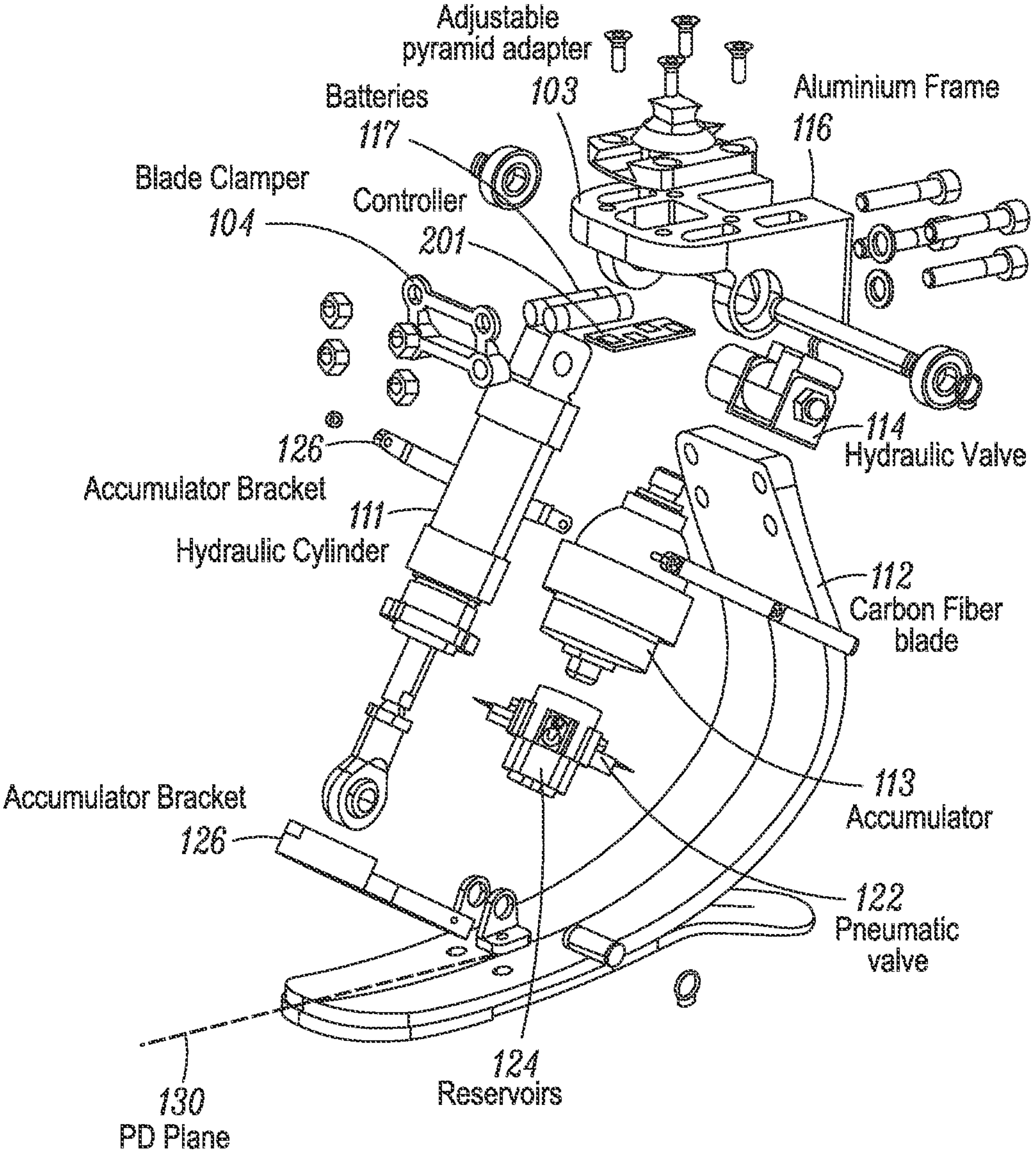
FIG. 1C is an image that illustrate an example of an exploded perspective view of the system of FIG. 1A, according to an embodiment.

FIGS. 1A through 1C are images that illustrate an example of a system 100 for enhancing an operation of a leg prothesis 150, according to an embodiment. In one embodiment, the leg prothesis 150 includes a first portion (e.g., semi-rigid blade 112) and a second portion (e.g., frame 116 and/or pylon attached to the frame). In an example embodiment, the frame 116 is secured to the leg of a user via a pyramid attachment 102 and pylon (e.g., at an amputation site). In one embodiment, the semi-rigid blade 112 is attached to the frame 116 (e.g., with a plurality of fasteners) such that the semi-rigid blade 112 and the frame 116 can rotate with respect to each other in a first plane. In an example embodiment, the system 100 is configured to rotate in the first plane (e.g., plantar-dorsiflexion plane or PD plane 130, see FIGS. 1B and 1C) such that the semi-rigid blade 112 and frame 116 can rotate with respect to each other in the first plane. In one example embodiment, the system 100 is configured to rotate only in the first plane such that the semi-rigid blade 112 and frame 116 can rotate with respect to each other only in the first plane. In another example embodiment, the semi-rigid blade 112 and frame 116 are configured to rotate with respect to each other in more than one plane (e.g., PD plane 130 and a second plane orthogonal to the PD plane 130). As appreciated by one of ordinary skill in the art, during operation of the leg prothesis 150, the pylon and/or frame 116 and the semi-rigid blade 112 rotate with respect to each other in the first plane (e.g., PD plane 130) based on a combination of effort of the user and ground reaction forces during the gait phases of the user. In other embodiments, the variable stiffness mechanism disclosed herein can be used with other assistive devices (e.g., exoskeletal device, ankle foot orthoses, etc.)

In an embodiment, an apparatus 110 is provided to enhance the operation of the leg prothesis 150. In one embodiment, the apparatus 110 excludes the leg prothesis 150. In an example embodiment, the apparatus 110 is a kit that can be installed on an existing leg prothesis to enhance the operation of an existing leg prothesis (e.g., provide adjustable stiffness to the leg prothesis based on movement conditions) and thus convert the existing leg prothesis into an improved leg prothesis. In another example embodiment, the system 100 includes the apparatus 110 and the leg prothesis 150.

Figure 1D:
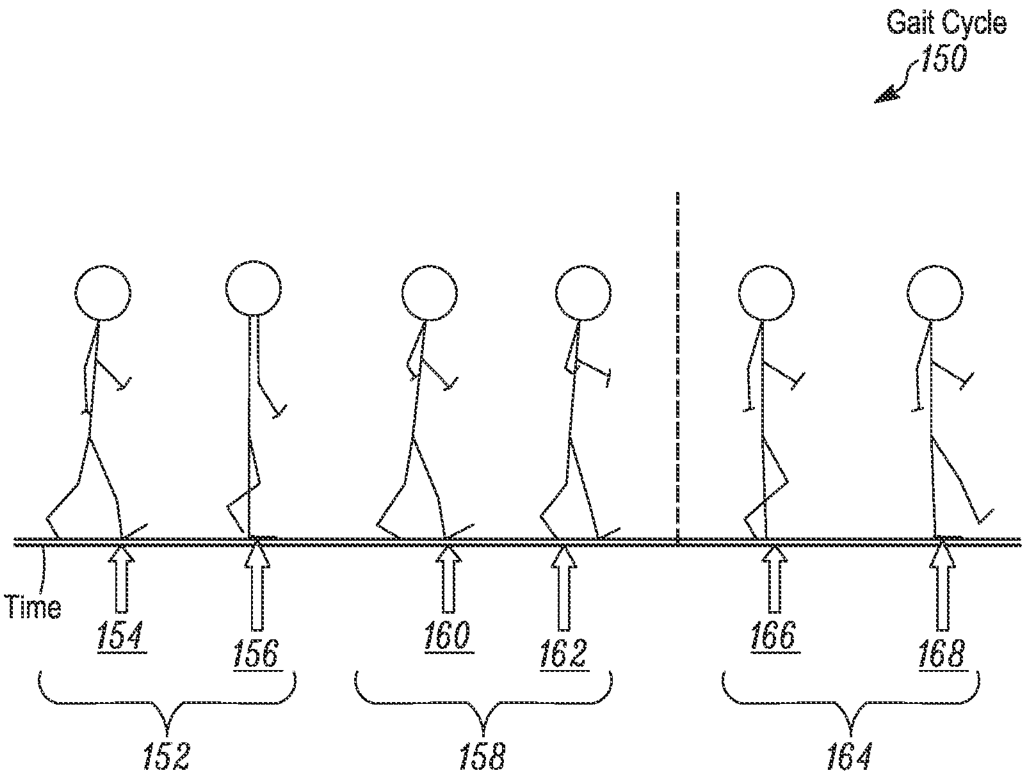
FIG. 1D is a diagram of a plurality of movement phases of a gait cycle of a subject, according to an embodiment.

In an embodiment, the apparatus 110 includes a variable stiffness module configured to be attached between the first portion (e.g., semi-rigid blade 112) and the second portion (e.g., frame 116) of the leg prothesis 150. As appreciated by one of ordinary skill in the art, different conditions of movement of the leg prothesis 150 (e.g., different gait phase, different speed, different incline, different surface, different gait phase, etc.) require different stiffness levels of the leg prothesis 150. FIG. 1D is a diagram of a plurality of movement phases of a gait cycle 150 of a subject, according to an embodiment. The gait cycle 150 begins with an early stance 152 which includes a heel strike movement phase 154 and a mid stance movement phase 156. The gait cycle 150 then proceeds to a late stance 158, which include a heel off movement phase 160, and a toe off movement phase 162. The gait cycle 150 then proceeds to a swing 164 that includes an initial swing movement phase 166 and a terminal swing movement phase 168. In some embodiments, different stiffness levels are provided based on different movement phases of the gait cycle 150. In other embodiments, different stiffness levels are provided based on different speed, such as a running condition requiring a greater stiffness level in the leg prothesis 150 relative to a walking condition. In some embodiments, the apparatus 110 is calibrated by measuring the stiffness levels of the apparatus 110 at different known movement phases, known speeds, etc. In these embodiments, one or more sensors are used to measure the stiffness level of the apparatus 110. These stiffness levels are then stored in a memory of the controller 201 of the system 100 and are utilized during operation of the system 100.

In an embodiment, the variable stiffness module defines an interior region (not shown in FIGS. 1A through 1C) configured to store pressurized fluid. In this embodiment, a volume of the interior region is configured to vary from a first volume to a second volume such that a stiffness of the variable stiffness module in the first plane is varied from a first stiffness to a second stiffness. In one embodiment, the variable stiffness module includes a linear actuator with a first end coupled to the first portion of the leg prothesis 150. In an example embodiment, the linear actuator is a hydraulic cylinder 111 with the first end rotatably coupled to the semi-rigid blade 112 at a hinge 120. In one example embodiment, the first end is rotatably coupled to the hinge 120 which is a preexisting fastener of a conventional blade (e.g., Cheetah®, Ottobock, Berlin, Germany) to link the hydraulic cylinder 111 to the leg prothesis 150.

In this embodiment, the linear actuator also includes a second end coupled to the second portion of the leg prothesis 150. In an example embodiment, the second end of the hydraulic cylinder 111 is rotatably coupled to the frame 116 at a hinge 118. In this embodiment, movement of the semi-rigid blade 112 relative to the frame 116 displaces a piston within the hydraulic cylinder 111 and consequently displaces a first fluid (e.g., hydraulic fluid) within the hydraulic cylinder 111. In an example embodiment, since the first and second ends of the hydraulic cylinder 111 are pivotally coupled to the semi-rigid blade 112 and the frame 116, the hydraulic cylinder 111 is configured to rotate within the first plane based on movement of the blade 112 relative to the frame 116 in the first plane. Although some embodiments disclose that the variable stiffness module is a linear actuator and in other embodiments the linear actuator is a hydraulic cylinder, in still other embodiments the variable stiffness module is not limited to a linear actuator and includes springs.

In one embodiment, the apparatus 110 further includes an accumulator 113 in flow communication with the linear actuator (e.g., hydraulic cylinder 111) to receive the displaced first fluid from the linear actuator and to pressurize a second fluid within the interior region. In some embodiments, the first fluid and second fluid are different (e.g., first fluid is hydraulic fluid and the second fluid is pneumatic fluid). In other embodiments, the first fluid and the second fluid are the same fluid (e.g., hydraulic fluid or pneumatic fluid). In one embodiment, a pneumatic manifold is implemented directly onto the accumulator 113 to reduce the need for piping, to reduce the design complexity and further reduce a risk of leakage. In this embodiment, pneumatic parts (e.g., the reservoir 124 and the pneumatic valves 122) will be mounted onto the accumulator 113 through the manifold to make the design compact (FIGS. 1A and 1C). As shown in FIG. 1A, in one embodiment, the accumulator 113 is positioned between the linear actuator (e.g., hydraulic cylinder 111) and the blade 112. The inventors of the present invention recognized that this arrangement advantageously achieves a low profile and a compact size and/or saves space and thus enhances the compactness and portability of the system (e.g., to fit in the shoe of a user). As shown in FIGS. 1A and 1B, the system 100 has a height of about 258 millimeters (mm) or in a range from about 200 mm to about 300 mm; has a depth of about 266 mm or in a range from about 200 mm to about 300 mm; and has a width of about 85 mm or in a range from about 50 mm to about 150 mm. However, the system is not limited to these particular dimensional ranges.

In one embodiment, the linear actuator (e.g., hydraulic cylinder 111) is attached to the hinges 118, 120 such that it is oriented at an angle relative to the first portion (e.g., portion of the blade 112 that contacts a ground surface) and/or relative to a ground surface, where the angle is about 60 degrees or in a range from about 45 degrees to about 75 degrees or from about 25 degrees to about 75 degrees. The inventors of the present invention recognized that this orientation of the hydraulic cylinder 111 attached to the system further enhances the spatial efficiency of the system (e.g., so the apparatus can fit in the shoe of a user). In an embodiment, the angle is chosen based on certain factors. For example, if the angle is too small, the force will not transmit to the cylinder and prosthesis. In this example embodiment, the inventors recognized that selecting the angle within a range from about 25 degrees to about 75 degrees would effectively transmit this force to the cylinder and prothesis.

In an embodiment, the carbon fiber blade 112 of the passive prosthesis 150 bears most of the force in its deformation, allowing the hydraulic cylinder 111 to modulate the stiffness by increasing it an additional amount (e.g., about 20% or in a range from about 10% to about 30%). In some embodiments, the percentage that the stiffness is modulated can be wider if a bigger size cylinder is used that can manage higher pressure. However, in these embodiments, the bigger size cylinder will increase the overall size and weight of the prothesis.

In one embodiment, the frame 116 of the leg prothesis 150 is an aluminum frame. As shown in FIG. 1A, a pyramid attachment 102 is secured to the frame 116 and is used to attach the leg prothesis 150 to one or more components (e.g., pylon) to secure the leg prothesis 150 to a leg of the user. As shown in FIG. 1C, in one embodiment, the pyramid attachment 102 can be moved on the frame 116 with an adjustable pyramid adapter 103 (e.g., that facilitates sliding the pyramid attachment 102 in one or more dimensions along the frame 116). In an example embodiment, the adjustable pyramid adapter 103 is selected such that the pyramid attachment 102 can shift anteriorly or posteriorly when it is mounted to the top of the device (e.g., to the frame 116) and one third of the prosthetic blade to allow a prosthetist to prescribe a custom fit to the people with lower limb amputation.

In an embodiment, the goals of the design of the system 100 are to develop an affordable, lightweight ankle prosthesis which adjusts the stiffness and energy release timing of ankle joint during walking. In one embodiment, the variable stiffness module (e.g., hydraulic cylinder 111 and accumulator 113) is capable of increasing the stiffness (e.g., up to about 20%) of the commercially available compliant passive prosthetic blade. Since the prosthetic blade 112 provides a basis of stiffness, the variable stiffness module has a compact, lightweight size (e.g., about 1.4 kg), and aesthetically pleasing exterior that fits inside the user's shoe. In an example embodiment, both a hydraulic and a pneumatic system (e.g., hydraulic cylinder 111 and pneumatic actuator 113) are employed to control the level of stiffness and energy return timing of an ankle foot prosthesis. In an example embodiment, the design of the device combines a standard of care compliant stiffness passive prosthesis and a hydraulic cylinder (e.g., DSNU-32-20-P-S11®, Festo, Esslingen, Germany) to make the prosthesis compact in size and lightweight.

Figure 2A:
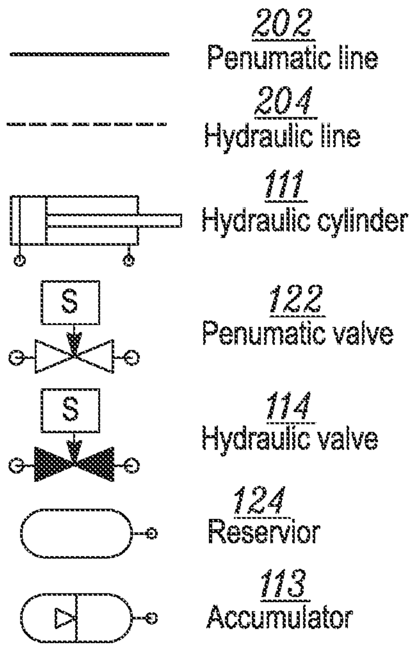
FIG. 2A is an image that illustrates an example of components of the apparatus of FIG. 1A, according to an embodiment.
Figure 2B:
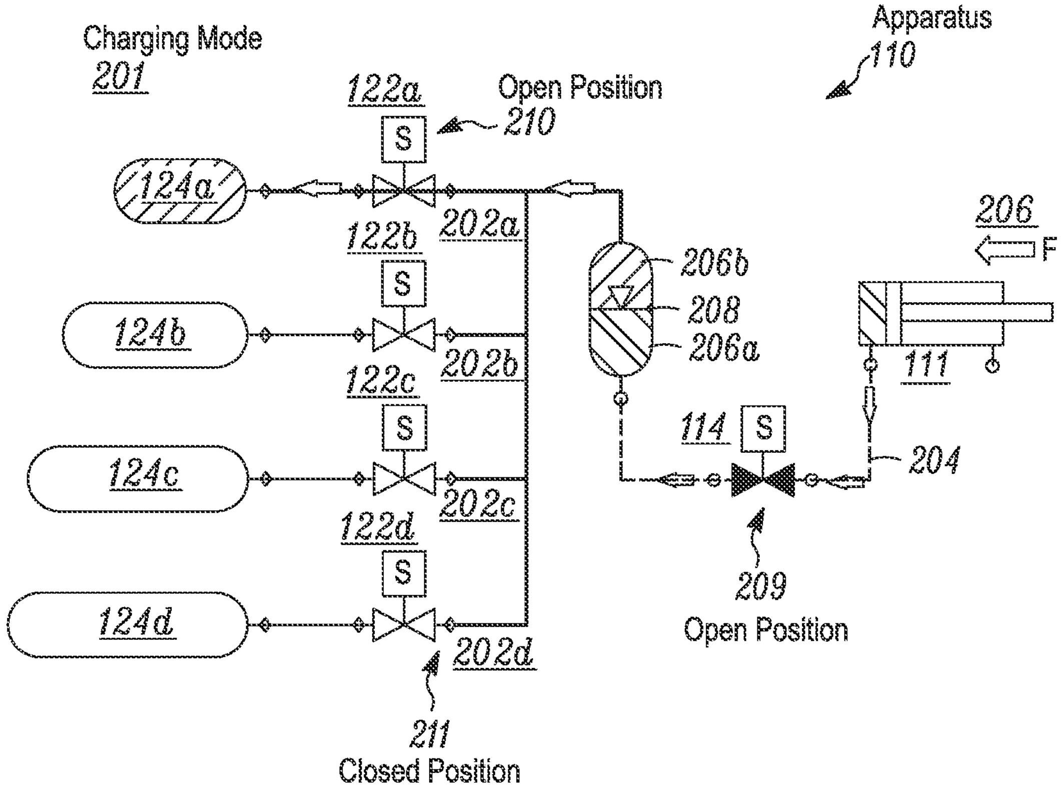
FIG. 2B is an image that illustrates an example of components of the apparatus of FIG. 1A in a charging mode, according to an embodiment.

FIGS. 2A through 2D are images that illustrate an example of components of the apparatus of FIG. 1A, according to an embodiment. As shown in FIG. 2B, the accumulator 113 includes a pair of chambers 206*a*, 206*b* separated by a diaphragm 208 such that the first chamber 206*a* is configured to receive the first fluid (e.g., hydraulic fluid) from the linear actuator (e.g., hydraulic cylinder 111). The accumulator 113 also includes the second chamber 206*b* configured to store a second fluid (e.g., pneumatic fluid). The diaphragm 208 is configured to displace upon receiving the first fluid in the first chamber 206*a* to reduce a volume of the second chamber 206*b* and thus pressurize the second fluid in the interior region. For purposes of this description, "interior region" means the collective volume for storing the second fluid.

As shown in FIG. 2B, in some embodiments, the interior region includes a plurality of reservoirs 124*a* through 124*d* that are configured to collectively store the second fluid. The reservoirs 124*a* through 124*d* are in flow communication with the accumulator 113 (with the second chamber 206*b*) through respective valves 122*a* through 122*d*. In this embodiment, the volume of the interior region is the volume of the second chamber 206*b* and the volume of any of the reservoirs 124*a* through 124*d* in flow communication with the second chamber 206*b* (e.g., where the respective valves 122*a* through 122*d* of those chambers are in an open position 210). Additionally, the volume of the interior region excludes any of the reservoirs 124*a* through 124*d* that are not in flow communication with the second chamber 206*b* (e.g., where the respective valves 122*a* through 122*d* are in the closed position 211). Although FIG. 2B depicts a plurality of reservoirs 124*a* through 124*d*, in other embodiments only one reservoir or greater than four reservoirs are provided. Additionally, although FIG. 2B depicts that the volume of each respective reservoir 124*a* through 124*d* varies, in other embodiments one or more of the reservoirs have the same volume.

In an embodiment, the linear actuator is the hydraulic cylinder 111 including a piston, where the first fluid is hydraulic fluid such that movement of the first portion (e.g., blade 112) relative to the second portion (e.g., frame 116) causes the piston to displace the hydraulic fluid. In this embodiment, the accumulator 113 is in flow communication with the hydraulic cylinder 111 through a hydraulic valve 114. The first chamber 206*a* of the accumulator 113 is configured to receive the hydraulic fluid from the hydraulic cylinder 111 when the hydraulic valve 114 is in an open position 209 (FIG. 2B). In this embodiment, the second fluid is pneumatic fluid such that the second chamber 206*b* is configured to store the pneumatic fluid based on displacement of the diaphragm 208 of the accumulator 113 upon the hydraulic fluid being received in the first chamber 206*a*.

In an example embodiment, as the user moves from a first gait phase (e.g., heel strike movement phase 154) to a second gait phase (e.g., mid stance movement phase 156), the weight of the body deforms the prosthetic blade 112, displacing the piston towards the hinge 118. This pushes hydraulic fluid out of the piston and into the accumulator 113, compressing air within the system. During a subsequent third gait phase (e.g., toe off movement phase 162), the pressurized air in hydraulic cylinder 111 applies force to the carbon fiber blade 112 by pushing the head of piston from the hinge 118 to the hinge 120. In this embodiment, this energy return supports and propels the body during walking.

In an embodiment, the first fluid is compressible fluid (e.g., pneumatic fluid) used in the interior region (e.g. second chamber 206*b* and reservoirs 124) since it can be compressed to act as a spring to restore energy. In this embodiment, the second fluid is incompressible fluid (e.g., hydraulic fluid) that is not used in the interior region since it cannot be compressed to restore energy in this manner. In this embodiment, incompressible fluid (e.g., hydraulic fluid) is used on the other side of the accumulator 113 (e.g. in the first chamber 206*a* and piping 204).

Figure 2C:
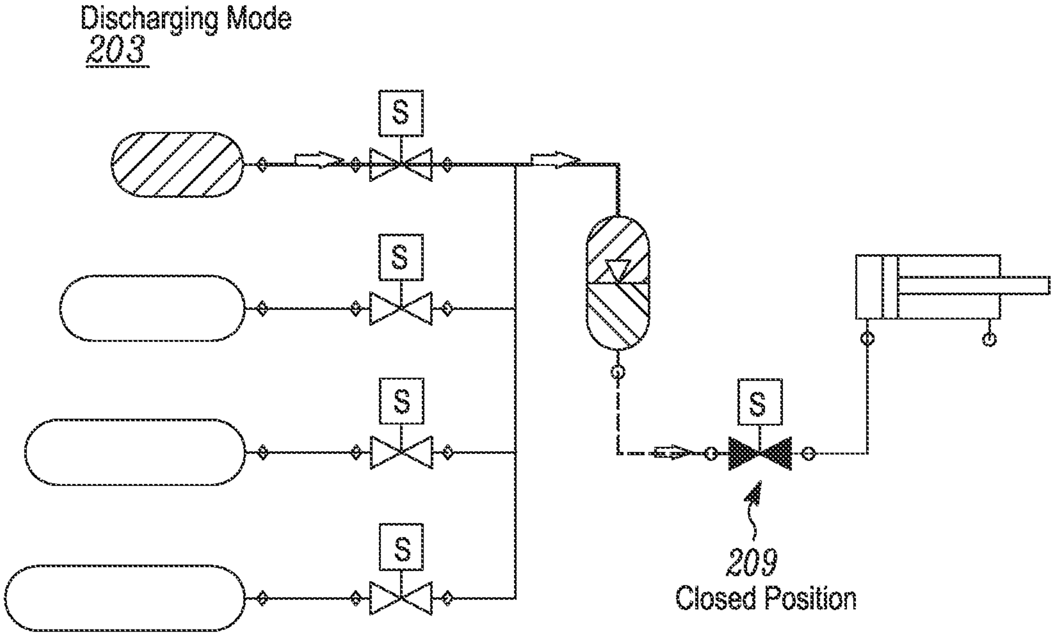
FIGS. 2C and 2D are images that illustrate an example of components of the apparatus of FIG. 1A in a discharging mode, according to an embodiment.
Figure 2D:
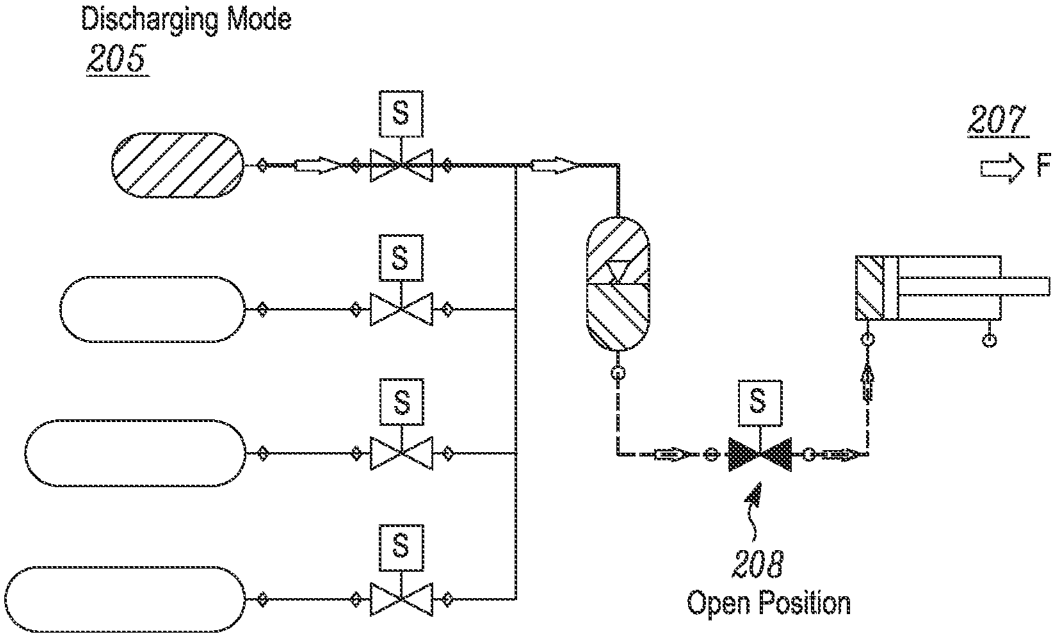

In an embodiment, as the user moves with the leg prosthesis 150, the system 100 alternates between states: a charging mode 201 (FIG. 2B) and a first discharging mode 203 (FIG. 2C) and a second discharging mode 205 (FIG. 2D). During the charging mode 201 (FIG. 2B), energy from the body's movement is first converted into hydraulic energy and then into pneumatic energy where it is stored in the reservoirs 124. As the user moves from a first gait phase (e.g., heel strike movement phase 154) to a second gait phase (e.g., mid stance movement phase 156) the cylinder 111 is compressed by dorsiflexion of the prosthetic leg 150, pushing oil into the accumulator 113 (FIG. 2B). The first chamber 206*a* is a fluid chamber and the second chamber 206*b* is an air chamber separated by the diaphragm 208.

A level of stiffness of the apparatus 110 is based on an volume of the interior region (e.g. collective volume for storing the second fluid). Thus, in some embodiments, the level of stiffness of the apparatus 110 is varied by varying the volume of the interior region. As fluid flows into the accumulator 113, the diaphragm 208 is displaced, reducing the volume of the air chamber 206*b* and pressurizing it. The total initial volume of the contained air (interior region) depends on the states of the shut-off pneumatic valves 122*a* through 122*d* to different sized reservoir chambers 124*a* through 124*d*. Different combinations of available reservoirs 124*a* through 124*d* correspond to different initial volumes for the accumulator 113 (different interior region volumes). For example, if all shut off valves 122*a* through 122*d* are closed, then only the volume of accumulator (volume of the chamber 206*b*) will be pressurized by movements within the hydraulic system 100. On the other hand, when all shut off valves 122*a* through 122*d* are open, associated with the maximum total volume, the sensitivity of pressure to displacement from the hydraulic system 100 is minimized. In an example embodiment, with four unique reservoirs 124*a* through 124*d*, sixteen different combinations of initial volume are available corresponding to sixteen different stiffness levels of the prosthesis 150. In the example embodiment of FIG. 2B, only one reservoir 124*a* is used to adjust the stiffness level based on opening the valve 122*a* and closing the other valves 122*b* through 122*d*. In an example embodiment, if the other valves 122*b* through 122*d* were opened, this would reduce the pressure to the accumulator 113 (e.g., reduced pressure in the second chamber 206*b*) leading to a decrease in the stiffness of the hydraulic cylinder 111.

During the first discharging mode 203 (FIG. 2C), after the deformation of the foot, energy held by the accumulator 113 is stored by moving the hydraulic valve 114 to a closed position 207 (FIG. 2C). The stored energy is then returned to the prosthetic foot 150 during the second discharging mode 205 (FIG. 2D) when the hydraulic valve 114 is moved to an open position 209. Thus, the energy return timing of the leg prothesis 150 can be modulated. In an example embodiment, during the first discharging mode 203 of FIG. 2C the hydraulic valve 114 is moved to the closed position 207 (e.g., during midstance movement phase 156) to delay energy return to the leg prosthesis 150. In another example embodiment, during the second discharging mode 205 of FIG. 2D, the hydraulic valve 114 is moved to the open position 209 to return the stored energy to the leg prosthesis 150 (e.g., during toe off movement phase 162).

Figure 2E:
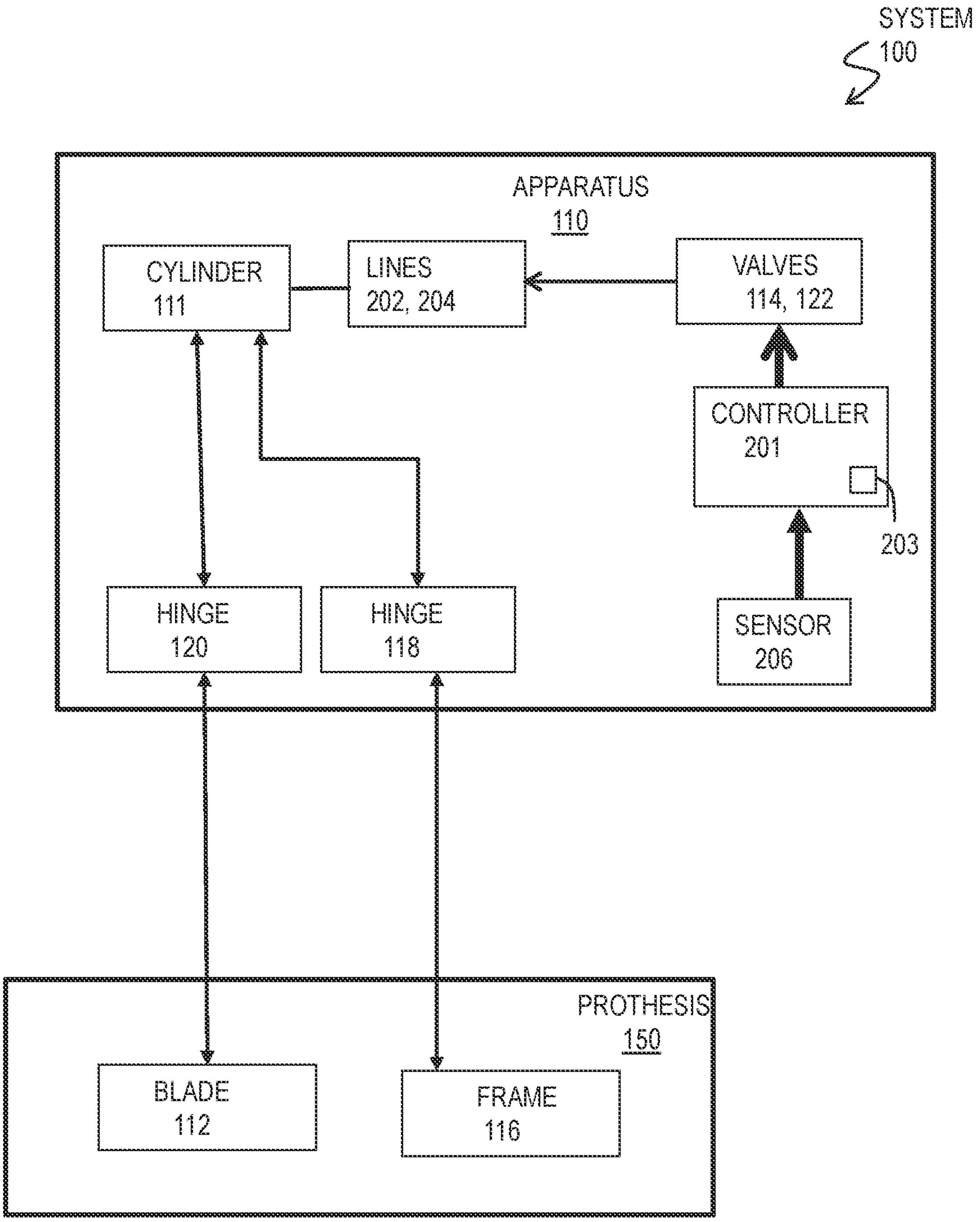
FIG. 2E is a block diagram that illustrates the components of the system of FIG. 1A, according to an embodiment.

FIG. 2E is a block diagram that illustrates the components of the system 100 of FIG. 1A, according to an embodiment. Thin lines (1.5 point) in FIG. 2E indicate mechanical coupling between components of the system and thick lines (3.5 point) indicate communicative coupling between the components of the system. In an embodiment, the apparatus 110 of the system 100 includes the controller 201, such as a computer system 400 described below with reference to FIG. 4, a chip set 500 described below with reference to FIG. 5 or a mobile terminal 600 described below with reference to FIG. 6. A memory 203 of the controller 201 includes instructions to perform one or more steps of the method 300 based on the flowchart of FIG. 3.

In an embodiment, the apparatus 110 includes a sensor 206 configured to measure a value of a parameter that indicates a condition of movement (e.g., a gait phase, one or more of a speed, an incline, a surface of movement, etc.) of a user wearing the legal prothesis 150. In an example embodiment, the sensor 206 is an inertial measurement unit (IMU). In other embodiments, sensors 206 other than an IMU can be used, such as a load cell and a potentiometer that can measure the force and stroke displacement of the cylinder can be used to identify various motions. In an embodiment, the controller 201 is configured to transmit a signal to the valves 112, 114 to move one or more of the valves 112, 114 to an open or closed position. In an embodiment, the controller 201 is a controller board with an embedded sensor 206 (e.g., IMU sensor). In this embodiment, FIGS. 1A through 1C depict the controller 201 and a power source (e.g., battery 117) that supplies power to the controller 201 and the embedded sensor 206. In an example embodiment, the controller 201 and power source (e.g., battery 117) are fixedly mounted to the frame 116. In an example embodiment, the sensor 206 (e.g., IMU sensor) embedded on the controller 201 is configured to measure one or more of a current movement phase (e.g., heel strike movement phase 154, mid stance movement phase 156, etc.) and/or a motion condition (e.g. running, walking, etc.) and/or a motion parameter (e.g. value of a speed). In this example embodiment, the appropriate valve (e.g., valve 122*a* through 122*d*) are opened/closed during the appropriate swing phase detected by the sensor 206 and/or based on any changes in motion condition detected by the sensor 206 (e.g. subject starts running after walking, etc.) This arrangement would be fixed during the stance phase.

In an embodiment, the controller 201 is communicatively coupled to the sensor 206 and the valves 114, 122. During operation of the system, the sensor 206 measures the value of the parameter (e.g., value of an acceleration measured by the IMU sensor due ground forces enacted on the leg prothesis 150 at one or more time increments) and transmits a first signal indicating the value of the parameter to the controller 201. In an example embodiment, the sensor 206 measures the value of the parameter that indicates one or more of a speed value, an incline angle value, a gait movement phase and a surface of movement of the user wearing the leg prothesis 150.

In one embodiment, the controller 201 receives the first signal from the sensor 206 indicating the value of the parameter. The controller 201 determines a desired level of stiffness based on the received value of the parameter from the sensor 206 and/or further determines a desired position of each valve 114, 122 to achieve the desired level of stiffness in the cylinder 111. In an example embodiment, the memory 203 of the controller 201 stores first data that indicates a desired level of stiffness of the cylinder 111 in the first plane based on the value of the parameter and/or second data that indicates a desired position of each valve 114, 122 (e.g., charging mode 201 of FIG. 2B, discharging mode 203 of FIG. 2C or discharging mode 205 of FIG. 2C) to achieve the desired level of stiffness in the cylinder 111. In one embodiment, upon determining a desired position of each valve 114, 122, the controller 201 transmits a second signal to the valves 114, 122 to move the valves 114, 122 to the appropriate position (open or closed) such that the desired level of stiffness in the cylinder 111 is achieved.

In an example embodiment, upon the controller 201 receiving the first signal from the sensor 206 indicating a gait phase of movement of the user, the controller 201 determines a desired level of stiffness (e.g., from data in the memory 203) based on the gait phase. In an example embodiment, where the controller 201 determines that the first signal from the sensor 206 indicates that the user is moving from a heel strike movement phase 154 to a midstance movement phase 156, the controller 201 transmits a signal to the valves 114, 122 to achieve the charging mode 201 arrangement of FIG. 2B. In an example embodiment, where the controller 201 determines that the first signal from the sensor 206 indicates that the user is in the midstance movement phase 156, the controller 201 transmits a signal to the valves 114, 122 to achieve the first discharging mode 203 arrangement of FIG. 2C. In an example embodiment, where the controller 201 determines that the first signal from the sensor 206 indicates that the user is in a toe off movement phase 162, the controller 201 transmits a signal to the valves 114, 122 to achieve the second discharging mode 205 arrangement of FIG. 2D.

Figure 1E:
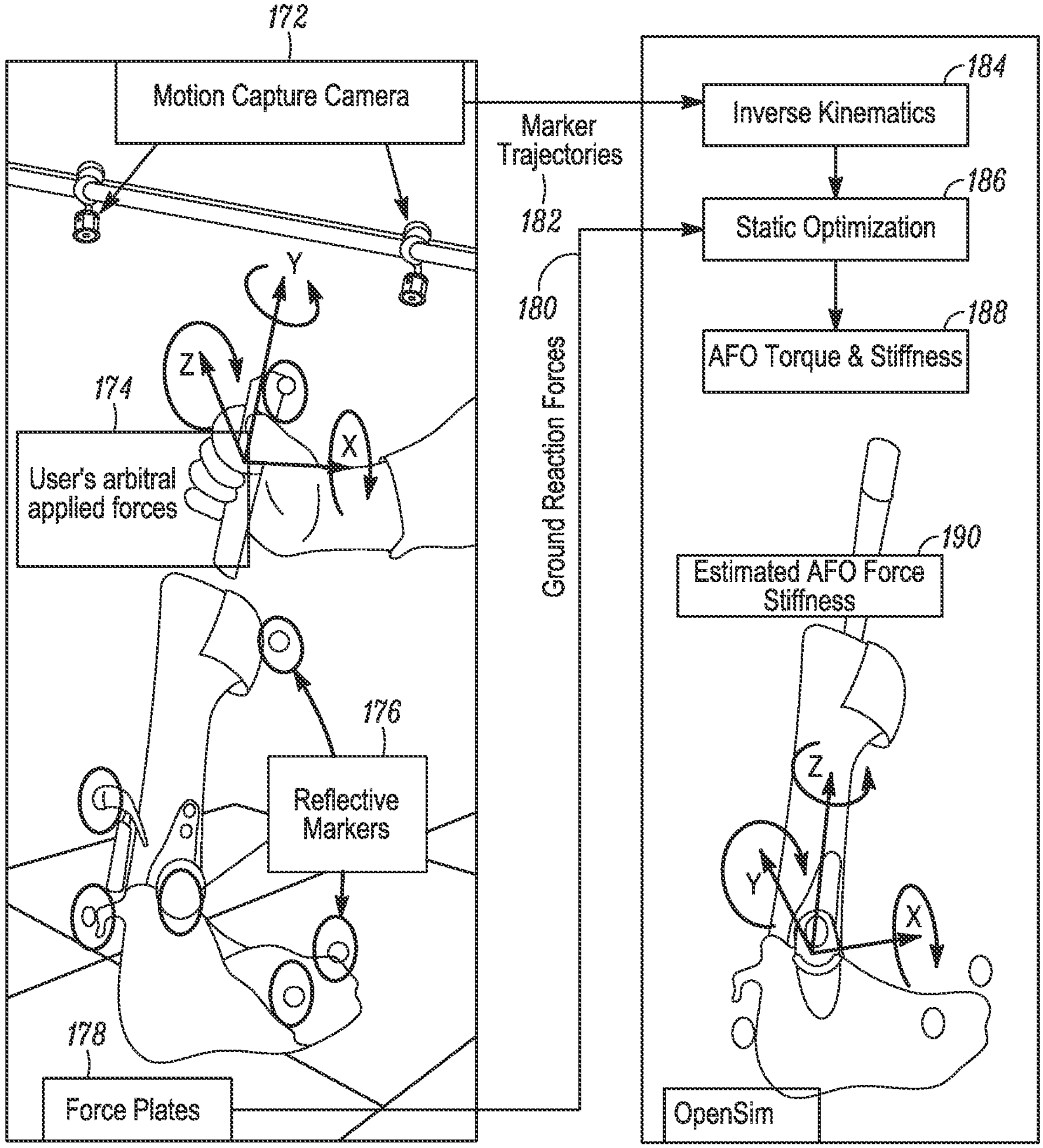
FIG. 1E is an image that illustrate an example of a system used to calibrate the stress of the blade of the system of FIG. 1A, according to an embodiment.

In some embodiments, the desired level of stiffness that is stored in the memory 203 is determined in various ways. In one embodiment, the desired level of stiffness is based on determining a level of stiffness attributable to the blade 112 based on the measured parameter from the sensor 206 (e.g. movement phase in the gait cycle 150, speed, etc.). In this embodiment, the level of stiffness of the blade 112 is determined by gathering first data (e.g., that indicates deformation of the blade 112) and second data (e.g., that indicates an amount of ground reaction force imparted by the blade 112 on the ground). In these embodiments, this first data and second data are combined in order to determine the level of stiffness attributed to the blade 112 based on the measured parameter from the sensor 206 (e.g. movement phase of the gait cycle 150). FIG. 1E is an image that illustrate an example of a system 170 used to calibrate the stress of the blade 112 of the system 100 of FIG. 1A, according to an embodiment. The system 170 includes motion capture cameras 172 which are configured to gather image data indicating a position of reflective markers 176 mounted at various locations on the leg prothesis 150. As a user walks while wearing the leg prothesis 150, the user applies forces 174 which cause the various reflective markers 176 to change positions as the user walks through the movement phases of the gait cycle 150. The motion capture cameras 172 collect this image data (e.g., indicating the position of the reflective markers 176) and send this data 182 to an inverse kinematics module 184. As the user walks through the gait cycle 150, force plates 178 on the ground measure the applied forces 174 and send this second data indicating the measured force data to a static optimization module 186. In these embodiments, the first data 182 (image data indicating the position of the reflective markers 176) and the second data 180 (force data) are combined at a AFO Torque and stiffness module 188 to determine the level of stiffness attributable to the leg prothesis 150 at each movement phase of the gait cycle 150 [17].

In an example embodiment, to determine target stiffness levels for the design of the system, a participant was tested with unilateral transtibial amputation (e.g., age 37, weight 107 kg, K-level 4) to determine the range of stiffness for the system. The participant walked on overground force plates 178 (FIG. 1E) (Optima™®, AMTI, Watertown, MA) at a self-selected speed with a passive ankle prosthesis that provided an appropriate stiffness at normal walking speeds [14] (Pro-flex XC Torsion®, Catagory: 8, Össur, Reykjavik, Iceland) [15]. The movements of the participant and the prosthetic foot were tracked using a motion capture system 172 and reflective markers 176 installed on the prosthetic foot (FIG. 1E) (Vicon, Oxford, UK) and measured ground reaction forces from the force plates 178. Then, the level of stiffness of the participant's prosthesis were quantified from first data 182 (the measured deformation of prosthetic blade) and second data 180 (ground reaction forces) to select the range of stiffness. In an example embodiment, since the variable stiffness module (e.g., apparatus 110 including the hydraulic and pneumatic control unit) will be installed in parallel with the carbon fiber foot blade 112, the carbon fiber foot blade 112 stiffness must also be accounted for. Since the foot blade 112 has complex geometry, it is challenging to identify accurate stiffness profile with deformation. Thus, in one example embodiment an Ankle Assistive Device Stiffness (AADS) algorithm is employed with a testing method that was designed for evaluating ankle foot orthosis stiffness to evaluate the prosthetic stiffness (FIG. 1E). In this example embodiment, the AADS testing enables the quick, easy, and nondestructive measure of device ankle stiffness in a gait lab. The AADS test uses an optimization algorithm [17] that finds device stiffness by modeling users' six degree of freedom bending force 174. For this, the motion capture system 172 is used to measure the deformation of the carbon fiber prosthetic foot blade 112 and force plates 178 (AMTI) to measure six degree of freedom of ground reaction 174 data while users simply apply a force to bend the prosthetic foot. The acquired carbon fiber prosthetic foot blade stiffness data will be combined with the stiffness data of the pneumatic-hydraulic hybrid module to identify the entire stiffness range and torque-angle curve of the device.

Figure 1F:
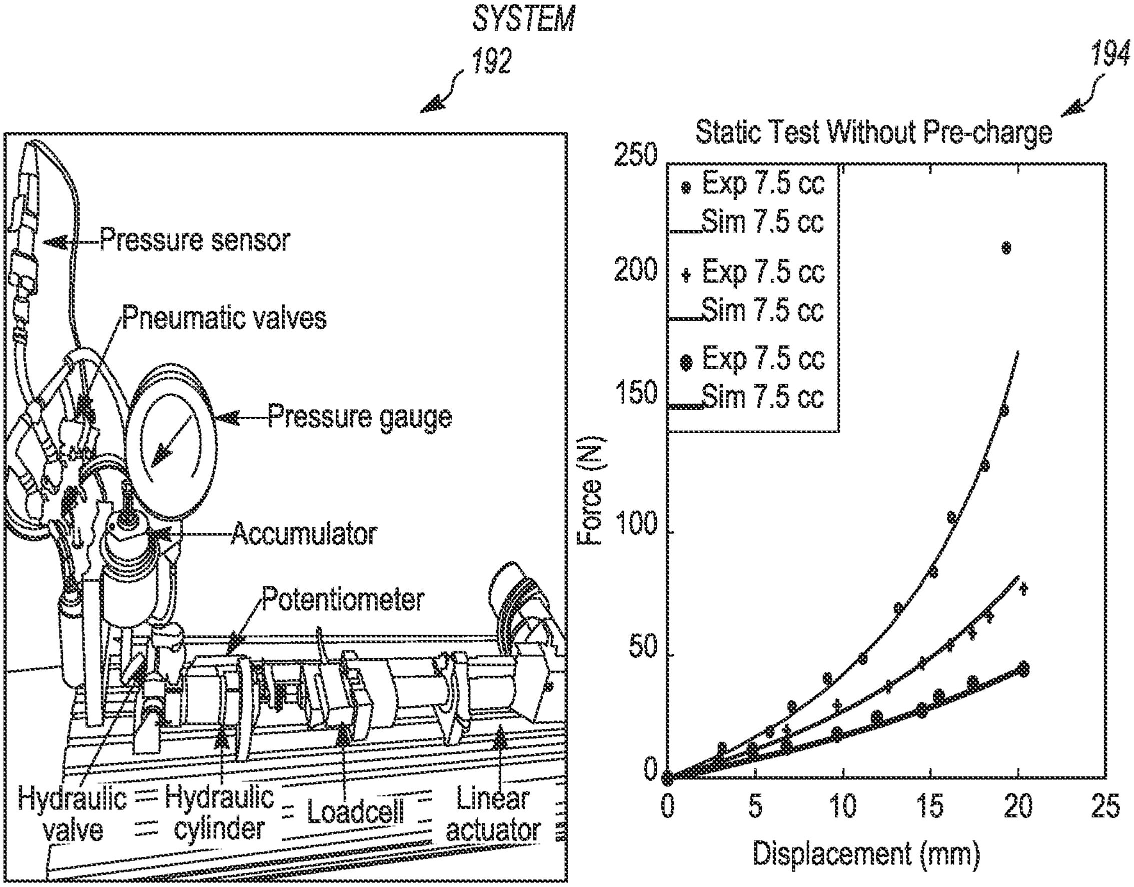
FIG. 1F is an image that illustrate an example of a system used to calibrate the stress of the variable stiffness module of the system of FIG. 1A, according to an embodiment.

In an embodiment, the desired level of stiffness that is stored in the memory 203 is based on not only the stiffness level attributable to the blade 112 but also the stiffness level attributable to the variable stiffness module (e.g. apparatus 110). In this embodiment, the desired stiffness level stored in the memory 203 is based on both the stiffness level attributable to the blade 112 and the stiffness level attributable to the variable stiffness module. Since the level of participant's prosthesis is prescribed for the normal walking speed, the stiffness required to achieve an ideal range of +/−10% of original stiffness was determined, intended to facilitate slow and fast walking speeds [16]. In an example embodiment, the design increases prosthetic stiffness, and thus a more compliant passive prosthesis was employed (Cheetah, Ottobock, Berlin, Germany) than the participants' prosthesis to set the minimum stiffness level. In this example embodiment, to generate greater levels of stiffness, the hydraulic cylinder 111 was installed on the prosthetic blade 112. FIG. 1F is an image that illustrate an example of a system 192 used to calibrate the stress of the variable stiffness module of the system 100 of FIG. 1A, according to an embodiment. In some embodiments, the stiffness attributable to the variable stiffness module is determined using a theoretical model or by calibrating the relationship between the interior volume and stiffness. In an embodiment 192 includes various components (e.g. pressure sensor, pressure gauge, etc.) that are used to calibrate the variable stiffness module, such that the interior volume of the variable stiffness is module is varied and the resulting pressure or force is measured for each interior volume value. Since the opening of one or more valves 114, 122 changes the interior volume value, this calibration establishes a relationship between the opening or closing of valves 114, 122 (interior volume value) and the stiffness of the variable stiffness module. This data can then be used to generate the graph 194. The horizontal axis is displacement (in millimeters, mm) of the linear actuator and the vertical axis is the measured stiffness or force (in newtons N). Since this calibration provides actual system response, this calibration data can be used during operation of the system 100 so that the apparatus 110 stiffness corresponds to a desired level of stiffness. In an example embodiment, the desired stiffness level stored in the memory 203 is based on this calibrated stiffness attributed to the apparatus 110 and the calibrated stiffness attributable to the blade 112. During operation of the system 100, the sensor 206 measures a parameter (e.g. movement phase, speed, etc) and the desired stiffness level corresponding to this measured parameter is retrieved from the memory 203. The controller 201 then opens one or more of the valves 114, 122 in order to achieve the desired level of stiffness. This calibration data of the apparatus 110 indicates which valves 114, 122 are to be open to achieve a desired level of stiffness.

Figure 3:
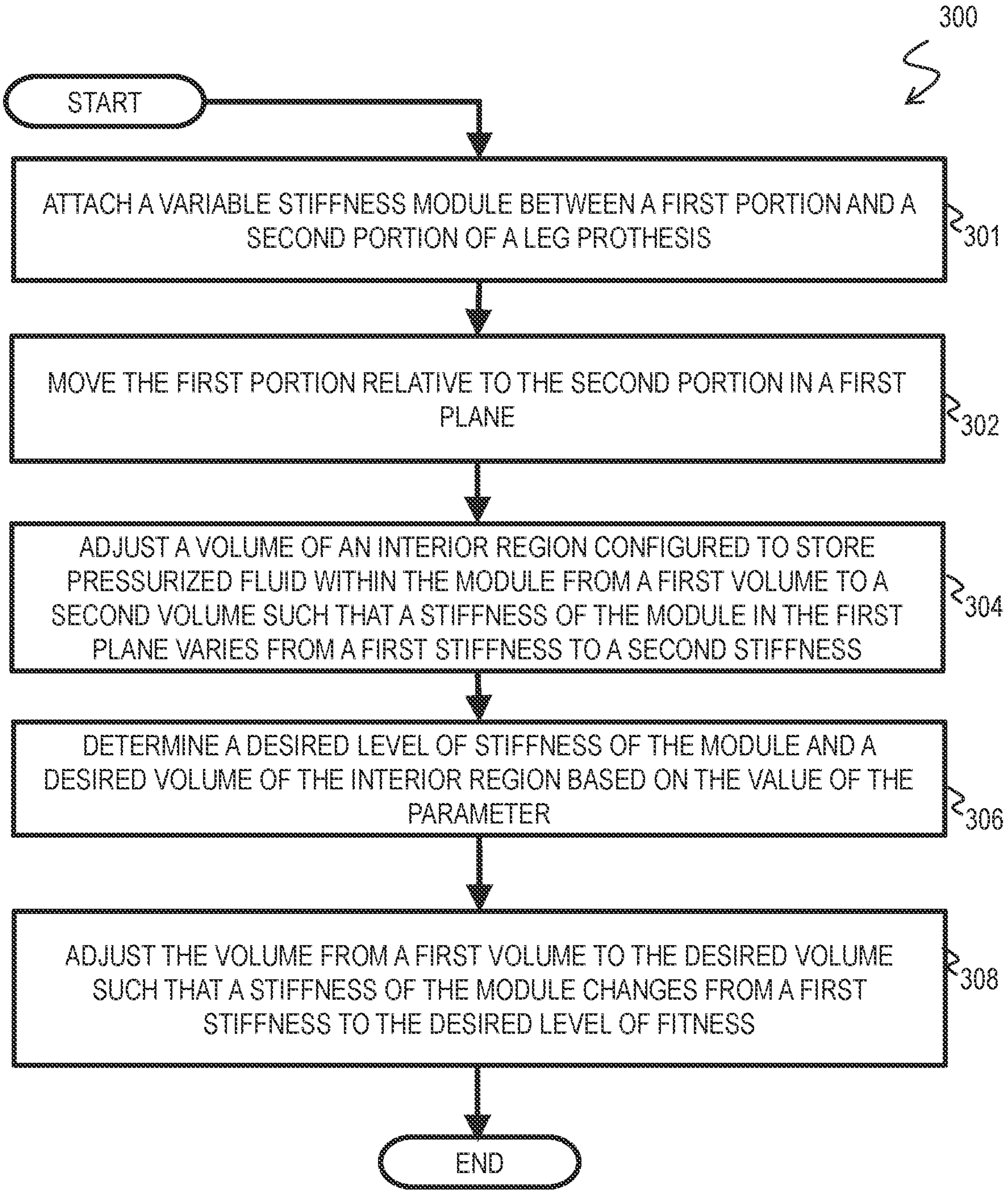
FIG. 3 is a flow chart that illustrates an example method for enhancing an operation of a leg prothesis of FIG. 1A, according to an embodiment.

FIG. 3 is a flow chart that illustrates an example method 300 for enhancing the operation of a leg prothesis. Although steps are depicted in FIG. 3 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 301, the variable stiffness module (e.g., hydraulic cylinder 111) is attached between the first portion and the second portion of the leg prothesis 150. In one embodiment, in step 301 the hydraulic cylinder 111 is attached between the blade 112 and the frame 116 of the system 100. In an example embodiment, in step 301 the hydraulic cylinder 111 is mounted with the hinge 118 to the blade 112 and with the hinge 120 to the frame 116.

In step 302, the first portion of the leg prothesis is moved relative to the second portion of the leg prothesis in the first plane. In an embodiment, after attaching the leg prothesis 150 to the user in step 301, in step 302 the user initiates a gait cycle with the leg prothesis 150 along a surface. In an example embodiment, in step 302 the blade 112 moves within the PD plane 130 relative to the frame 116 and/or the pylon (e.g., due to effort of the user and/or ground reaction forces).

In step 304, a value of a parameter is measured that indicates a condition of movement of the leg prothesis 150 in step 302. In one embodiment, in step 304 the value of the parameter is measured by the sensor 206. In an example embodiment the parameter includes is one or more of speed, incline, surface of movement, gait movement phase and any other parameter that can be used to characterize a movement of the leg prothesis 150 (e.g., characterize a gait phase). In an example embodiment the sensor 206 is an IMU sensor and/or is configured to measure a current gait movement phase of the leg prothesis 150 at incremental time periods. In an example embodiment, in step 304 the sensor 206 transmits a first signal to the controller 201 that indicates the value of the parameter (e.g., the current movement phase of the gait cycle).

In step 306, a desired level of stiffness for the cylinder is determined based on the value of the parameter measured in step 304. In one embodiment, in step 306 a desired volume of the interior region (e.g., volume of the pneumatic fluid based on the second chamber 206*b* and one or more of the reservoirs 124*a* through 124*d*) is determined based on the desired level of stiffness of the cylinder 111 and/or the value of the parameter (e.g., the current movement phase of the gait cycle). In one embodiment, in step 306 a desired position of the valves 114, 122 (e.g., one of the charging mode 201, first discharging mode 203 and second discharging mode 205) is determined based on the desired level of stiffness and/or the value of the parameter. The position of the valves 114, 122 is adjusted to adjust the volume of the interior region (for the second fluid). In an example embodiment, the memory 203 of the controller 201 stores first data that indicates the desired level of stiffness (e.g., based on the value of the parameter and/or the current movement phase of the gait cycle) and/or second data that indicates the desired position of the valves 114, 122 (e.g., charging mode 201, discharging mode 203 or discharging mode 205). In an embodiment, in step 306 the controller 201 receives the first signal from the sensor 206 and uses the measured value of the parameter to determine the desired level of stiffness and/or desired position of the valves 114, 122 to achieve the desired level of stiffness.

In an example embodiment, the first data and the second data are obtained during a calibration process, e.g., where the leg prothesis 150 is moved at different conditions of movement (e.g., different speeds, different inclines, etc.) and the level of stiffness of the hydraulic cylinder 111 is measured at different positions of the valves 114, 122 (e.g., different interior region volumes). The position of the valves 114, 122 at which the desired level of stiffness in the cylinder 111 is attained is stored in the memory 203 for each movement condition (e.g., for each gait phase). In an example embodiment, the desired level of stiffness is known for different conditions of movement.

In step 308, the volume of the interior region is adjusted from a first volume to a desired volume such that the stiffness of the cylinder 111 is the desired level of stiffness from step 306. In this embodiment, in step 308 one or more of the valves 114, 122 are moved from a first position to a second position (e.g., desired position) such that the stiffness of the cylinder 111 in the second position is the desired level of stiffness determined in step 306.

In an embodiment, the method 300 includes a loop which repeats steps 302 through 308. For each loop of steps 304 through 308, if the movement condition of the leg prothesis (step 304) does not change, then no action is taken in steps 306 and 308.

2. Hardware Overview

Figure 4:
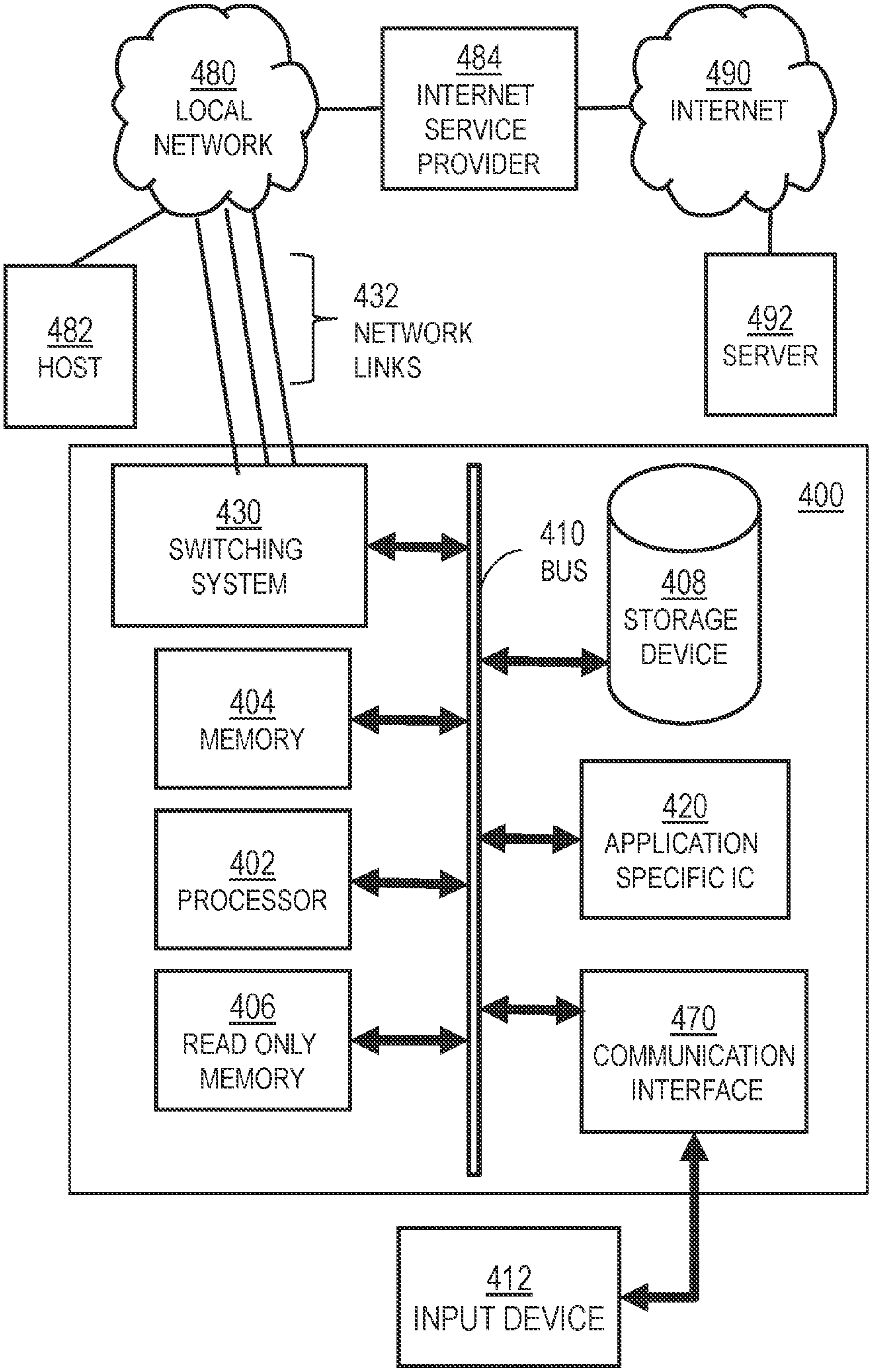
FIG. 4 is a block diagram that illustrates a computer system upon which an embodiment of the invention may be implemented.

FIG. 4 is a block diagram that illustrates a computer system 400 upon which an embodiment of the invention may be implemented. Computer system 400 includes a communication mechanism such as a bus 410 for passing information between other internal and external components of the computer system 400. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 400, or a portion thereof, constitutes a means for performing one or more steps of one or more methods described herein.

A sequence of binary digits constitutes digital data that is used to represent a number or code for a character. A bus 410 includes many parallel conductors of information so that information is transferred quickly among devices coupled to the bus 410. One or more processors 402 for processing information are coupled with the bus 410. A processor 402 performs a set of operations on information. The set of operations include bringing information in from the bus 410 and placing information on the bus 410. The set of operations also typically include comparing two or more units of information, shifting positions of units of information, and combining two or more units of information, such as by addition or multiplication. A sequence of operations to be executed by the processor 402 constitutes computer instructions.

Computer system 400 also includes a memory 404 coupled to bus 410. The memory 404, such as a random access memory (RAM) or other dynamic storage device, stores information including computer instructions. Dynamic memory allows information stored therein to be changed by the computer system 400. RAM allows a unit of information stored at a location called a memory address to be stored and retrieved independently of information at neighboring addresses. The memory 404 is also used by the processor 402 to store temporary values during execution of computer instructions. The computer system 400 also includes a read only memory (ROM) 406 or other static storage device coupled to the bus 410 for storing static information, including instructions, that is not changed by the computer system 400. Also coupled to bus 410 is a non-volatile (persistent) storage device 408, such as a magnetic disk or optical disk, for storing information, including instructions, that persists even when the computer system 400 is turned off or otherwise loses power.

Information, including instructions, is provided to the bus 410 for use by the processor from an external input device 412, such as a keyboard containing alphanumeric keys operated by a human user, or a sensor. A sensor detects conditions in its vicinity and transforms those detections into signals compatible with the signals used to represent information in computer system 400. Other external devices coupled to bus 410, used primarily for interacting with humans, include a display device 414, such as a cathode ray tube (CRT) or a liquid crystal display (LCD), for presenting images, and a pointing device 416, such as a mouse or a trackball or cursor direction keys, for controlling a position of a small cursor image presented on the display 414 and issuing commands associated with graphical elements presented on the display 414.

In the illustrated embodiment, special purpose hardware, such as an application specific integrated circuit (IC) 420, is coupled to bus 410. The special purpose hardware is configured to perform operations not performed by processor 402 quickly enough for special purposes. Examples of application specific ICs include graphics accelerator cards for generating images for display 414, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 400 also includes one or more instances of a communications interface 470 coupled to bus 410. Communication interface 470 provides a two-way communication coupling to a variety of external devices that operate with their own processors, such as printers, scanners and external disks. In general, the coupling is with a network link 478 that is connected to a local network 480 to which a variety of external devices with their own processors are connected. For example, communication interface 470 may be a parallel port or a serial port or a universal serial bus (USB) port on a personal computer. In some embodiments, communications interface 470 is an integrated services digital network (ISDN) card or a digital subscriber line (DSL) card or a telephone modem that provides an information communication connection to a corresponding type of telephone line. In some embodiments, a communication interface 470 is a cable modem that converts signals on bus 410 into signals for a communication connection over a coaxial cable or into optical signals for a communication connection over a fiber optic cable. As another example, communications interface 470 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 470 sends and receives electrical, acoustic or electromagnetic signals, including infrared and optical signals, that carry information streams, such as digital data.

The term computer-readable medium is used herein to refer to any medium that participates in providing information to processor 402, including instructions for execution. Such a medium may take many forms, including, but not limited to, non-volatile media, volatile media and transmission media. Non-volatile media include, for example, optical or magnetic disks, such as storage device 408. Volatile media include, for example, dynamic memory 404. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 402, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 402, except for carrier waves and other signals.

Logic encoded in one or more tangible media includes one or both of processor instructions on a computer-readable storage media and special purpose hardware, such as ASIC *420.

Network link 478 typically provides information communication through one or more networks to other devices that use or process the information. For example, network link 478 may provide a connection through local network 480 to a host computer 482 or to equipment 484 operated by an Internet Service Provider (ISP). ISP equipment 484 in turn provides data communication services through the public, world-wide packet-switching communication network of networks now commonly referred to as the Internet 490. A computer called a server 492 connected to the Internet provides a service in response to information received over the Internet. For example, server 492 provides information representing video data for presentation at display 414.

The invention is related to the use of computer system 400 for implementing the techniques described herein. According to one embodiment of the invention, those techniques are performed by computer system 400 in response to processor 402 executing one or more sequences of one or more instructions contained in memory 404. Such instructions, also called software and program code, may be read into memory 404 from another computer-readable medium such as storage device 408. Execution of the sequences of instructions contained in memory 404 causes processor 402 to perform the method steps described herein. In alternative embodiments, hardware, such as application specific integrated circuit 420, may be used in place of or in combination with software to implement the invention. Thus, embodiments of the invention are not limited to any specific combination of hardware and software.

The signals transmitted over network link 478 and other networks through communications interface 470, carry information to and from computer system 400. Computer system 400 can send and receive information, including program code, through the networks 480, 490 among others, through network link 478 and communications interface 470. In an example using the Internet 490, a server 492 transmits program code for a particular application, requested by a message sent from computer 400, through Internet 490, ISP equipment 484, local network 480 and communications interface 470. The received code may be executed by processor 402 as it is received or may be stored in storage device 408 or other non-volatile storage for later execution, or both. In this manner, computer system 400 may obtain application program code in the form of a signal on a carrier wave.

Various forms of computer readable media may be involved in carrying one or more sequence of instructions or data or both to processor 402 for execution. For example, instructions and data may initially be carried on a magnetic disk of a remote computer such as host 482. The remote computer loads the instructions and data into its dynamic memory and sends the instructions and data over a telephone line using a modem. A modem local to the computer system 400 receives the instructions and data on a telephone line and uses an infra-red transmitter to convert the instructions and data to a signal on an infra-red a carrier wave serving as the network link 478. An infrared detector serving as communications interface 470 receives the instructions and data carried in the infrared signal and places information representing the instructions and data onto bus 410. Bus 410 carries the information to memory 404 from which processor 402 retrieves and executes the instructions using some of the data sent with the instructions. The instructions and data received in memory 404 may optionally be stored on storage device 408, either before or after execution by the processor 402.

Figure 5:
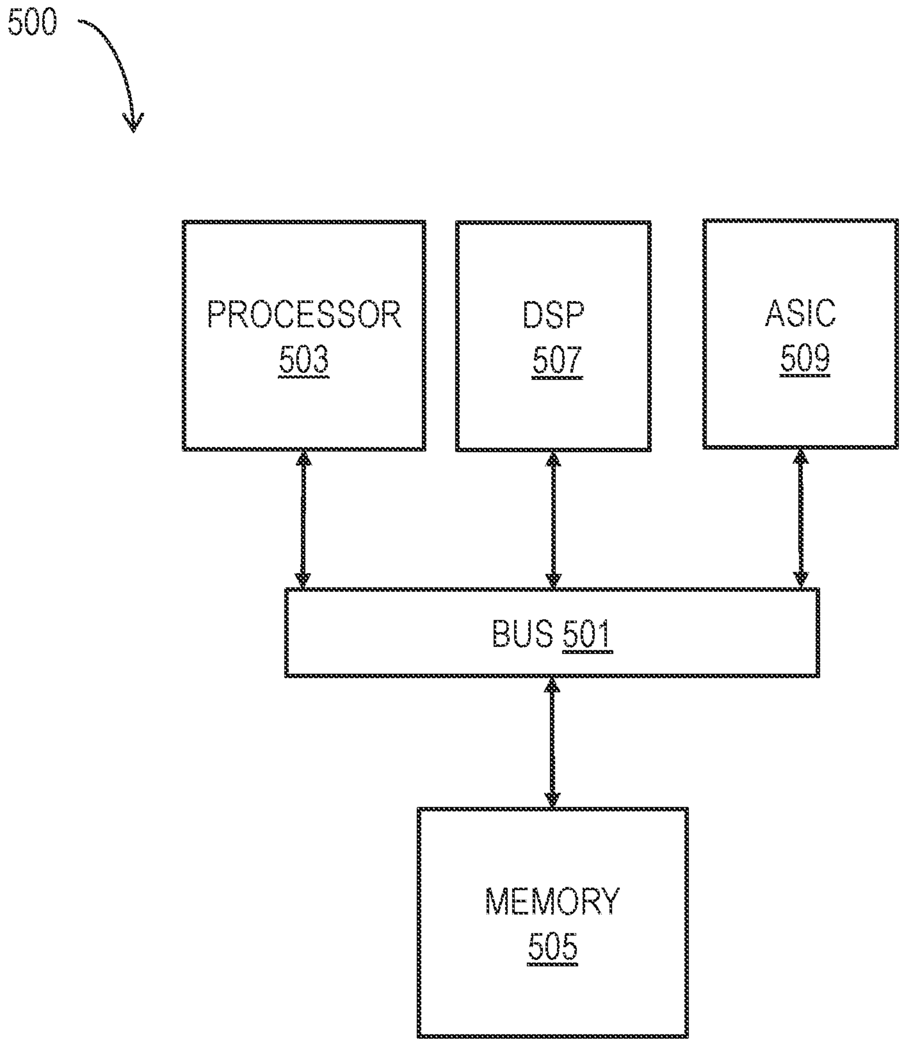
FIG. 5 illustrates a chip set upon which an embodiment of the invention may be implemented.

FIG. 5 illustrates a chip set 500 upon which an embodiment of the invention may be implemented. Chip set 500 is programmed to perform one or more steps of a method described herein and includes, for instance, the processor and memory components described with respect to FIG. *4 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 500, or a portion thereof, constitutes a means for performing one or more steps of a method described herein.

In one embodiment, the chip set 500 includes a communication mechanism such as a bus 501 for passing information among the components of the chip set 500. A processor 503 has connectivity to the bus 501 to execute instructions and process information stored in, for example, a memory 505. The processor 503 may include one or more processing cores with each core configured to perform independently. A multi-core processor enables multiprocessing within a single physical package. Examples of a multi-core processor include two, four, eight, or greater numbers of processing cores. Alternatively, or in addition, the processor 503 may include one or more microprocessors configured in tandem via the bus 501 to enable independent execution of instructions, pipelining, and multithreading. The processor 503 may also be accompanied with one or more specialized components to perform certain processing functions and tasks such as one or more digital signal processors (DSP) 507, or one or more application-specific integrated circuits (ASIC) 509. A DSP 507 typically is configured to process real-world signals (e.g., sound) in real time independently of the processor 503. Similarly, an ASIC 509 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 503 and accompanying components have connectivity to the memory 505 via the bus 501. The memory 505 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 505 also stores the data associated with or generated by the execution of one or more steps of the methods described herein.

Figure 6:
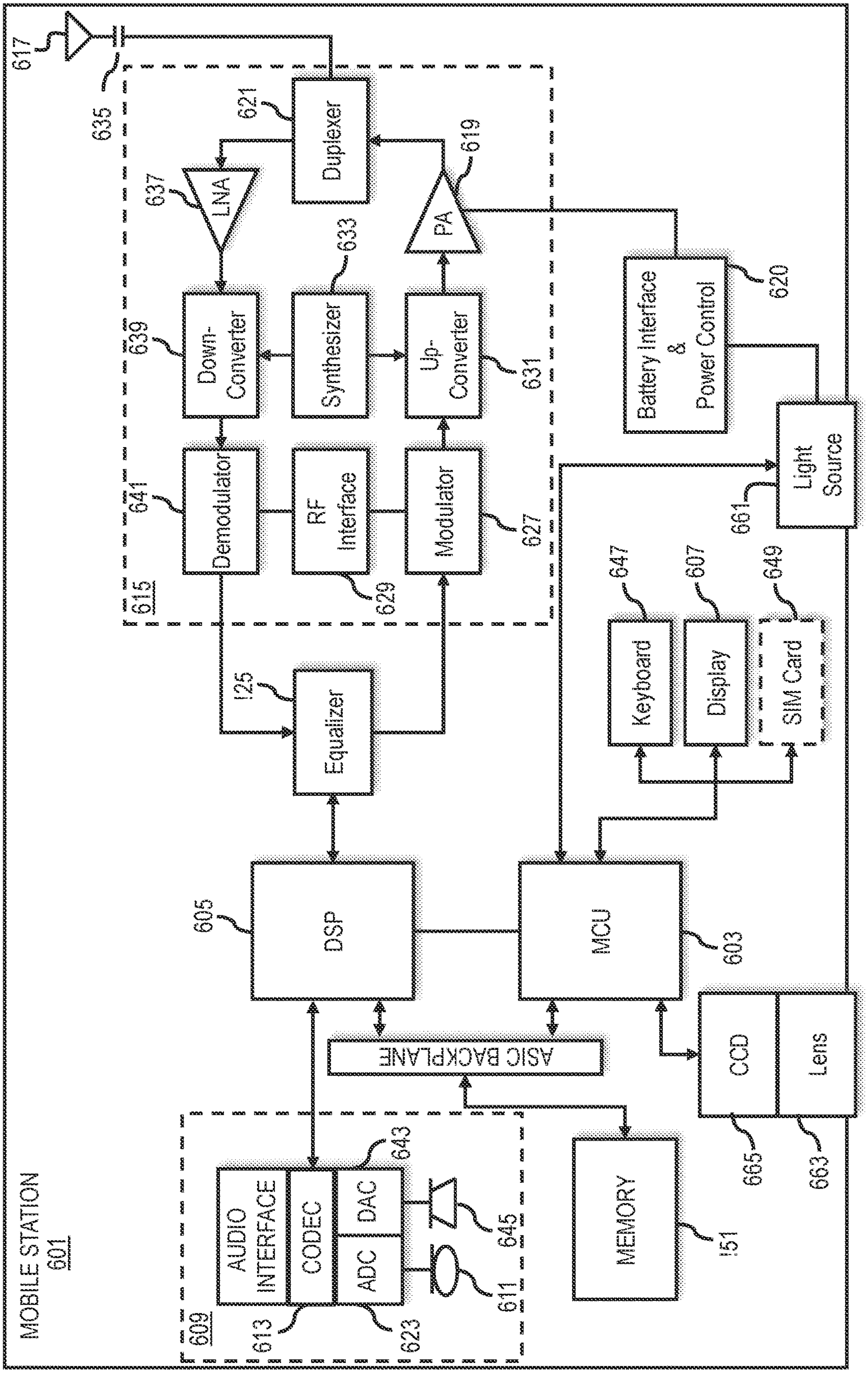
FIG. 6 illustrates a mobile terminal upon which an embodiment of the invention may be implemented.

FIG. 6 is a diagram of exemplary components of a mobile terminal 600 (e.g., cell phone handset) for communications, which is capable of operating in the system of FIG. 2C, according to one embodiment. In some embodiments, mobile terminal 601, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 603, a Digital Signal Processor (DSP) 605, and a receiver/transmitter unit including a microphone gain control unit and a speaker gain control unit. A main display unit 607 provides a display to the user in support of various applications and mobile terminal functions that perform or support the steps as described herein. The display 607 includes display circuitry configured to display at least a portion of a user interface of the mobile terminal (e.g., mobile telephone). Additionally, the display 607 and display circuitry are configured to facilitate user control of at least some functions of the mobile terminal. An audio function circuitry 609 includes a microphone 611 and microphone amplifier that amplifies the speech signal output from the microphone 611. The amplified speech signal output from the microphone 611 is fed to a coder/decoder (CODEC) 613.

A radio section 615 amplifies power and converts frequency in order to communicate with a base station, which is included in a mobile communication system, via antenna 617. The power amplifier (PA) 619 and the transmitter/modulation circuitry are operationally responsive to the MCU 603, with an output from the PA 619 coupled to the duplexer 621 or circulator or antenna switch, as known in the art. The PA 619 also couples to a battery interface and power control unit 620.

In use, a user of mobile terminal 601 speaks into the microphone 611 and his or her voice along with any detected background noise is converted into an analog voltage. The analog voltage is then converted into a digital signal through the Analog to Digital Converter (ADC) 623. The control unit 603 routes the digital signal into the DSP 605 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 625 for compensation of any frequency-dependent impairments that occur during transmission though the air such as phase and amplitude distortion. After equalizing the bit stream, the modulator 627 combines the signal with a RF signal generated in the RF interface 629. The modulator 627 generates a sine wave by way of frequency or phase modulation. In order to prepare the signal for transmission, an up-converter 631 combines the sine wave output from the modulator 627 with another sine wave generated by a synthesizer 633 to achieve the desired frequency of transmission. The signal is then sent through a PA 619 to increase the signal to an appropriate power level. In practical systems, the PA 619 acts as a variable gain amplifier whose gain is controlled by the DSP 605 from information received from a network base station. The signal is then filtered within the duplexer 621 and optionally sent to an antenna coupler 635 to match impedances to provide maximum power transfer. Finally, the signal is transmitted via antenna 617 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 601 are received via antenna 617 and immediately amplified by a low noise amplifier (LNA) 637. A down-converter 639 lowers the carrier frequency while the demodulator 641 strips away the RF leaving only a digital bit stream. The signal then goes through the equalizer 625 and is processed by the DSP 605. A Digital to Analog Converter (DAC) 643 converts the signal and the resulting output is transmitted to the user through the speaker 645, all under control of a Main Control Unit (MCU) 603 which can be implemented as a Central Processing Unit (CPU) (not shown).

The MCU 603 receives various signals including input signals from the keyboard 647. The keyboard 647 and/or the MCU 603 in combination with other user input components (e.g., the microphone 611) comprise a user interface circuitry for managing user input. The MCU 603 runs a user interface software to facilitate user control of at least some functions of the mobile terminal 601 as described herein. The MCU 603 also delivers a display command and a switch command to the display 607 and to the speech output switching controller, respectively. Further, the MCU 603 exchanges information with the DSP 605 and can access an optionally incorporated SIM card 649 and a memory 651. In addition, the MCU 603 executes various control functions required of the terminal. The DSP 605 may, depending upon the implementation, perform any of a variety of conventional digital processing functions on the voice signals. Additionally, DSP 605 determines the background noise level of the local environment from the signals detected by microphone 611 and sets the gain of microphone 611 to a level selected to compensate for the natural tendency of the user of the mobile terminal 601.

The CODEC 613 includes the ADC 623 and DAC 643. The memory 651 stores various data including call incoming tone data and is capable of storing other data including music data received via, e.g., the global Internet. The software module could reside in RAM memory, flash memory, registers, or any other form of writable storage medium known in the art. The memory device 651 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 649 carries, for instance, important information, such as the cellular phone number, the carrier supplying service, subscription details, and security information. The SIM card 649 serves primarily to identify the mobile terminal 601 on a radio network. The card 649 also contains a memory for storing a personal telephone number registry, text messages, and user specific mobile terminal settings.

In some embodiments, the mobile terminal 601 includes a digital camera comprising an array of optical detectors, such as charge coupled device (CCD) array 665. The output of the array is image data that is transferred to the MCU for further processing or storage in the memory 651 or both. In the illustrated embodiment, the light impinges on the optical array through a lens 663, such as a pin-hole lens or a material lens made of an optical grade glass or plastic material. In the illustrated embodiment, the mobile terminal 601 includes a light source 661, such as a LED to illuminate a subject for capture by the optical array, e.g., CCD 665. The light source is powered by the battery interface and power control module 620 and controlled by the MCU 603 based on instructions stored or loaded into the MCU 603.

3. ALTERNATIVES, DEVIATIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word “comprise” and its variations, such as “comprises” and “comprising,” will be understood to imply the inclusion of a stated item, element or step or group of items, elements or steps but not the exclusion of any other item, element or step or group of items, elements or steps. Furthermore, the indefinite article “a” or “an” is meant to indicate one or more of the item, element or step modified by the article.

4. REFERENCES

[1] P. DeVita, D. Hong, J. Hamill, “Effects of asymmetric load carrying on the biomechanics of walking”, in Journal of Biomechanics, 1991, pp. 1119-1129.

[2] Lauren A. Sepp, Erika Nelson-Wong, Brian S. Baum, Anne K. Silverman “Running-specific prostheses reduce lower-limb muscle activity compared to daily-use prostheses in people with unilateral transtibial amputations” in Journal of Electromyography and Kinesiology, pp. S1050-6411(20)30104-8,2020,

[3] R. D. Bellman, M. A. Holgate and T. G. Sugar, “SPARKy 3: Design of an active robotic ankle prosthesis with two actuated degrees of freedom using regenerative kinetics,” in {2008 2nd IEEE RAS \& EMBS International Conference on Biomedical Robotics and Biomechatronics, IEEE, 2008, pp. 511-516.

[4] M. Manchola, D. Serrano, D. Gömez, F. Ballen, D. Casas, M. Munera, C. A. Cifuentes “T-FLEX: Variable stiffness ankle-foot orthosis for gait assistance,” in International Symposium on Wearable Robotics, Springer, 2018, pp. 160-164.

[5] M. K. Shepherd and E. J. Rouse, “The VSPA Foot: A Quasi-Passive Ankle-Foot Prosthesis With Continuously Variable Stiffness,” in IEEE Transactions on Neural Systems and Rehabilitation Engineering, vol. 25, no. 12, pp. 2375-2386, December 2017, doi: 10.1109/TNSRE.2017.2750113.

[6] E. M. Glanzer and P. G. Adamczyk, “Design and Validation of a Semi-Active Variable Stiffness Foot Prosthesis,” in IEEE Transactions on Neural Systems and Rehabilitation Engineering, vol. 26, no. 12, pp. 2351-2359, December 2018, doi: 10.1109/TNSRE.2018.2877962.

[7] Ottobock, 2019, “Triton Smart Ankle,” Ottobock, Duderstadt, Germany, accessed Dec. 20, 2019, https://www.ottobock.com.tr/en/prosthetics/lower-limb/solution-overview/triton-smart-ankle/

[8] Blatchford, Inc., 2019, “Blatchford Elan Foot,” Blatchford, Miamisburg, OH, accessed Dec. 20, 2019, https://www.blatchfordus.com/products/elan/

[9] Freedom Innovations, 2019, “Freedom Innovations Kinnex,” Freedom Innovations, Irvine, CA, accessed Dec. 20, 2019, https://www.freedom-innovations.com/kinnex/

[10] Collins, Steven H., and Arthur D. Kuo. “Recycling energy to restore impaired ankle function during human walking.” PLoS one 5.2 (2010): e9307.

[11] Caldwell, Darwin G., Gustavo A. Medrano-Cerda, and Mike Goodwin. “Control of pneumatic muscle actuators.” IEEE Control Systems Magazine 15.1 (1995): 40-48.

[12] Mrazsko, Hannah, Jason Dekarske, and Peter Adamczyk. “Design of a Variable Stiffness Pneumatic Ankle Prosthesis with Self-Recharging for Weightlifting Exercise.” Journal of Medical Devices (2020).

[13] L. M. Mooney, C. H. Lai and E. J. Rouse, “Design and characterization of a biologically inspired quasi-passive prosthetic ankle-foot,” 2014 36th Annual International Conference of the IEEE Engineering in Medicine and Biology Society, Chicago, IL, 2014, pp. 1611-1617, doi: 10.1109/EMBC.2014.6943913

[14] Liu M Q, Anderson F C, Schwartz M H, Delp S L. Muscle contributions to support and progression over a range of walking speeds. J Biomech. 2008 Nov. 14;

41(15):3243-52. doi: 10.1016/j.jbiomech.2008.07.031. Epub 2008 Sep. 25. PMID: 18822415; PMCID: PMC4423744.

[15] https://www.ossur.com/en-us/prosthetics/feet/pro-flex-xc-torsion

[16] Li Jin, Michael E. Hahn, "Modulation of lower extremity joint stiffness, work and power at different walking and running speeds" in Human Movement Science, Pages 1-9, Volume 58, 2018, doi: 10.1016/j.humov.2018.01.004.

[17] I. Symeonidis, G. Kavadarli, E. Schuller and S. Peldschus, "Simulation of biomechanical experiments in OpenSim," *In XII Mediterranean Conference on Medical and Biological Engineering and Computing*, pp. 107-110, 2010.

What is claimed is:

1. An apparatus comprising:

a variable stiffness module configured to be attached between a first portion and a second portion of a leg prothesis wherein the first portion is configured to move relative to the second portion in a first plane;

wherein the variable stiffness module defines an interior region configured to store pressurized fluid and wherein a value of a volume of the interior region is configured to be varied from a first volume value to a second volume value such that a stiffness of the variable stiffness module in the first plane is varied from a first stiffness value to a second stiffness value;

wherein the variable stiffness module includes:

a linear actuator with a first end coupled to the first portion of the leg prothesis and a second end coupled to the second portion of the leg prothesis such that movement of the first portion relative to the second portion displaces a first fluid within the linear actuator; and an accumulator in flow communication with the linear actuator to receive the displaced first fluid from the linear actuator and to pressurize a second fluid that is the pressurized fluid within the interior region, wherein the second fluid is different from the first fluid.

2. The apparatus of claim 1, wherein the first portion is a blade;

wherein the apparatus is configured to control an energy release timing during a plurality of gait phases of a gait cycle based on a hydraulic valve between the linear actuator and the accumulator being in one of an open position or a closed position during each gait phase of the plurality of gait phases; and wherein the hydraulic valve is configured to be moved to the closed position during a midstance movement phase of the plurality of gait phases to delay energy return to the leg prothesis during the midstance movement phase based on the pressurized fluid within the interior region; and wherein the hydraulic valve is configured to be moved to the open position during a toe off movement phase of the plurality of gait phases to return stored energy to the leg prothesis during the toe off movement phase based on the pressurized fluid within the interior region.

3. The apparatus of claim 1, wherein the first fluid is a hydraulic fluid and wherein the second fluid is a pneumatic fluid.

4. The apparatus of claim 1, wherein the first portion is a blade of the leg prothesis and wherein the accumulator is positioned between the linear actuator and the blade.

5. The apparatus of claim 1, wherein the accumulator includes a pair of chambers separated by a diaphragm such that a first chamber of the pair of chambers is configured to receive the first fluid from the linear actuator and a second chamber of the pair of chambers is configured to store the second fluid, wherein the diaphragm is configured to displace upon receiving the first fluid in the first chamber to reduce a volume of the second chamber and pressurize the second fluid in the interior region.

6. The apparatus of claim 1, wherein the interior region includes a reservoir in flow communication with the accumulator through a valve such that the volume of the interior region is varied to include a volume of the reservoir when the valve is in an open position and exclude the volume of the reservoir when the valve is in a closed position.

7. The apparatus of claim 6, wherein a plurality of reservoirs are in flow communication with the accumulator through a respective plurality of valves such that the volume of the interior region is varied to include a volume of one or more first reservoirs when the respective valves of the one or more first reservoirs are in an open position and exclude a volume of one or more second reservoirs when the respective valves of the one or more second reservoirs are in a closed position.

8. The apparatus of claim 1, wherein the linear actuator is a hydraulic cylinder including a piston, wherein the first fluid is hydraulic fluid such that movement of the first portion relative to the second portion causes the piston to displace the hydraulic fluid;

wherein the accumulator is in flow communication with the hydraulic cylinder through a hydraulic valve, wherein the accumulator includes a pair of chambers separated by a diaphragm such that a first chamber of the pair of chambers is configured to receive the hydraulic fluid from the hydraulic cylinder when the hydraulic valve is in an open position;

wherein the second fluid is pneumatic fluid such that a second chamber of the pair of chambers is configured to store the pneumatic fluid based on displacement of the diagraph of the accumulator upon the hydraulic fluid being received in the first chamber.

9. The apparatus of claim 1, wherein the first end of the linear actuator is pivotally coupled to the first portion of the leg prothesis and wherein the second end of the linear actuator is pivotally coupled to the second portion of the leg prothesis such that the linear actuator is configured to rotate in the first plane based on movement of the first portion relative to the second portion.

10. The apparatus of claim 9, wherein the linear actuator is oriented at an angle relative to the first portion, wherein the angle is in a range from about 45 degrees to about 75 degrees.

11. The apparatus of claim 9, wherein the second portion of the leg prothesis is a frame of the leg prothesis, wherein the frame of the leg prothesis includes a pyramid configured to be attached to a pylon.

12. The apparatus of claim 1, wherein:

the value of the volume of the interior region is configured to be increased from the first volume to the second volume that is greater than the first volume such that the stiffness of the variable stiffness module in the first plane is reduced from the first stiffness value to the second stiffness value; and the value of the volume of the interior region is configured to be decreased from the first volume to the second volume that is less than the first volume such that the stiffness of the variable stiffness module in the first plane is increased from the first stiffness value to the second stiffness value.

13. A system comprising:

the apparatus of claim 1; and the leg prothesis including the first portion and the second portion.

14. The system of claim 13, wherein the first portion is configured to move relative to the second portion in only the first plane.

15. The system of claim 13, wherein the first portion is a blade and the second portion is a pylon of the leg prothesis.

16. A method comprising:

attaching a variable stiffness module between a first portion and a second portion of a leg prothesis;

moving, in a first plane, the first portion relative to the second portion including displacing a first fluid within a linear actuator, where a first end of the linear actuator is coupled to the first portion and a second end of the linear actuator is coupled to the second portion;

adjusting a value of a volume of an interior region configured to store pressurized fluid within the variable stiffness module from a first volume value to a second volume value such that a stiffness of the variable stiffness module in the first plane varies from a first stiffness value to a second stiffness value;

receiving, at an accumulator in flow communication with the linear actuator, the displaced first fluid; and pressurizing, with the accumulator, the pressurized fluid that is a second fluid within the interior region based on the receiving step, wherein the second fluid is different from the first fluid.

17. The method of claim 16, further comprising:

measuring, with a first sensor, a value of a parameter that indicates a condition of movement of a user during the moving of the first portion relative to the second portion;

transmitting, from the first sensor, a first signal to a controller indicating the value of the parameter;

determining, with the controller, a desired level of stiffness for the variable stiffness module and a desired volume of the interior region based on the value of the parameter, wherein the second volume is the desired volume and the second stiffness is the desired level of stiffness; and transmitting, from the controller, a second signal to a valve within the variable stiffness module to initiate the adjusting step from the first volume to the desired volume such that the stiffness of the variable stiffness module in the first plane varies from the first stiffness to the desired level of stiffness.

18. The method of claim 16, further controlling an energy release timing during a plurality of gait phases of a gait cycle based on moving a hydraulic valve between the linear actuator and the accumulator in one of an open position or a closed position during each gait phase of the plurality of gait phases, said moving step comprising:

moving the hydraulic valve to the closed position during a midstance movement phase of the plurality of gait phases to delay energy return to the leg prothesis during the midstance movement phase based on the pressurized fluid within the interior region; and moving the hydraulic valve to the open position during a toe off movement phase of the plurality of gait phases to return stored energy to the leg prothesis based on the pressurized fluid within the interior region.

19. An apparatus comprising:

a variable stiffness module configured to be attached between a first portion and a second portion of a leg prothesis wherein the first portion is configured to move relative to the second portion in a first plane;

wherein the variable stiffness module comprises:

an accumulator including a pair of chambers separated by a diaphragm such that a first chamber of the pair of chambers is configured to receive a first fluid based on movement of the first portion relative to the second portion and such that a second chamber of the pair of chambers is configured to store a second fluid; and an interior region in flow communication with the second chamber, wherein the diaphragm is configured to displace upon receiving the first fluid in the first chamber to pressurize the second fluid within the interior region.

20. The apparatus of claim 19, wherein a value of a volume of the interior region is configured to be varied from a first volume to a second volume such that a stiffness of the variable stiffness module in the first plane is varied from a first stiffness value to a second stiffness value upon pressurization of the second fluid within the interior region;

wherein the first fluid is a hydraulic fluid and the second fluid is a pneumatic fluid.

* * * * *